United States Patent
Okagami et al.

(10) Patent No.: US 10,792,102 B2
(45) Date of Patent: Oct. 6, 2020

(54) LASER TIP, LASER TREATMENT TOOL, LASER TREATMENT DEVICE, AND LASER TREATMENT SYSTEM

(71) Applicants: J. Morita Mfg. Corp., Kyoto (JP); National University Corp. Kobe University, Hyogo (JP)

(72) Inventors: Yoshihide Okagami, Kyoto (JP); Akihito Hongo, Kyoto (JP); Yoshiteru Tamura, Kyoto (JP); Katsumi Hiyoshi, Kyoto (JP); Haruhiko Murakami, Kyoto (JP); Takeshi Azuma, Hyogo (JP); Yoshinori Morita, Hyogo (JP)

(73) Assignees: J. Morita Mfg. Corp., Kyoto (JP); National University Corporation Kobe University, Hyogo (JP)

( * ) Notice: Subject to any disclaimer, the term of this patent is extended or adjusted under 35 U.S.C. 154(b) by 263 days.

(21) Appl. No.: 15/924,251

(22) Filed: Mar. 18, 2018

(65) Prior Publication Data
US 2018/0325595 A1 Nov. 15, 2018

(30) Foreign Application Priority Data

May 10, 2017 (JP) ................................. 2017-093830

(51) Int. Cl.
*A61B 18/22* (2006.01)
*A61B 17/29* (2006.01)
(Continued)

(52) U.S. Cl.
CPC .............. *A61B 18/22* (2013.01); *A61B 17/29* (2013.01); *A61B 2018/00023* (2013.01);
(Continued)

(58) Field of Classification Search
CPC ...................................................... A61B 18/22
See application file for complete search history.

(56) References Cited

U.S. PATENT DOCUMENTS

| 4,249,533 A | 2/1981 | Komiya |
| 5,441,489 A | 8/1995 | Utsumi et al. |

(Continued)

FOREIGN PATENT DOCUMENTS

| JP | 06-205789 A | 7/1994 |
| JP | 2004-321463 A | 11/2004 |
| WO | 93/21841 A1 | 11/1993 |

OTHER PUBLICATIONS

Communication under Article 94(3) EPC dated Nov. 19, 2019 issued by European Patent Office in EP 18 162 378.6 (4 pages).
(Continued)

*Primary Examiner* — Carl H Layno
*Assistant Examiner* — Jennifer L Ghand
(74) *Attorney, Agent, or Firm* — Capitol City TechLaw, PLLC; Samuel P. Burkholder

(57) ABSTRACT

A laser tip, a laser treatment tool, a laser treatment device and a laser treatment system are provided for performing laser treatment surgery and minimizing any bleeding. A laser tip is attachable to a laser radiation opening located at the tip end of a laser transmission tube. The laser tip includes an attaching portion detachable from the laser radiation opening and a contact portion contactable with biological tissue. The contact portion is at the front of the attaching portion in the direction in which the laser light exits the laser radiation opening. An open space is located between the contact portion and the attaching portion, and a coupler couples a part of the contact portion and a part of the attaching portion. The contact portion has a reflective surface at a rear end thereof which reflects the laser light toward the coupler.

15 Claims, 19 Drawing Sheets

(51) Int. Cl.
    *A61B 18/00*          (2006.01)
    *A61B 18/20*          (2006.01)
(52) U.S. Cl.
    CPC ............... *A61B 2018/00589* (2013.01); *A61B 2018/00595* (2013.01); *A61B 2018/00601* (2013.01); *A61B 2018/00607* (2013.01); *A61B 2018/00982* (2013.01); *A61B 2018/2035* (2013.01); *A61B 2018/2272* (2013.01); *A61B 2018/2285* (2017.05); *A61B 2218/002* (2013.01)

(56) References Cited

U.S. PATENT DOCUMENTS

| | | | | |
|---|---|---|---|---|
| 5,496,307 | A * | 3/1996 | Daikuzono | A61B 18/24 606/15 |
| 5,836,941 | A * | 11/1998 | Yoshihara | A61B 18/24 606/15 |
| 6,221,069 | B1 | 4/2001 | Daikuzono | |
| 2002/0161359 | A1* | 10/2002 | Yamamoto | A61B 18/201 606/19 |
| 2015/0057649 | A1 | 2/2015 | Lewinsky et al. | |

OTHER PUBLICATIONS

Extended European Search Report by European Patent Office for EP 18 16 2378 application dated Oct. 8, 2018 (9 pages).

* cited by examiner

LASER TIP, LASER TREATMENT TOOL, LASER TREATMENT DEVICE, AND LASER TREATMENT SYSTEM

CROSS-REFERENCE TO RELATED APPLICATIONS

This application is based upon and claims the benefit of priority from Japanese Patent Applications No. 2017-093830 filed on May 10, 2017, and No. 2017-224721 filed on Nov. 22, 2017, the entire contents all of which are incorporated herein by reference for all purposes.

BACKGROUND OF THE INVENTION

1. Field of the Invention

The present invention relates to a laser tip attachable to, for example, a tip end of a laser transmission tube, and a laser treatment tool, a laser treatment device and a laser treatment system each including the laser tip.

2. Description of the Prior Art

Recently, in the field of laparotomy, dental treatment or the like, a device for laser treatment using an electric knife, laser light or the like is used for a surgery. Minimally invasive medical practice using such a device has been developed. As an example of minimally invasive medical practice, treatments in surgery or internal medicine using an endoscope are now performed. Especially, endoscopic submucosal dissection (ESD) targeted for early stage digestive tract cancer attracts attention as an effective treatment method with little load on patients.

For example, the ESD mentioned above is performed as follows. First, a region including an affected site, which is a target of surgery, is marked, and this marking is used to dissect a mucosal layer. Next, a tissue in submucosa is peeled off, and all the tissues in the tumor are removed. For surgical operations of marking, dissection of the mucosal layer and peeling of the submucosa, a high-frequency electric knife is generally used as a treatment tool. Since there are blood vessels in the submucosa, there is a possibility that bleeding occurs during the surgery. In addition, for a surgery on colon or the like having an especially thin tissue wall, perforation may occur to the muscular layer outer to the submucosa, which may cause complications. Therefore, an operator of ESD needs to have a high level of skill.

For a treatment tool replacing the high-frequency electric knife, surgical methods using laser light effective for dissection of a biological tissue, hemostasis, coagulation and evaporation have been developed. Especially, carbon dioxide gas laser light is very highly absorbed by a biological tissue and water, and thus does not invade deep into the tissues. In the case where the carbon dioxide gas laser light is used, a normal tissue in the deep region is not damaged, and tissues are sequentially dissected from a surface layer irradiated with the laser light. As compared with the high-frequency electric knife conventionally used, use of the carbon dioxide gas laser light allows a surgery to be performed in a microscopic region while excessive thermal damage is suppressed.

In such a situation, a laser medical device that performs all the types of surgical operations, including hemostasis, by use of laser light with no need to change the energy source during the surgery has been developed. Various laser tips attachable to a laser radiation opening have been proposed. For example, Patent Document 1 discloses a plurality of laser tips each of which is attachable to a tip end of the laser radiation opening and absorbs the laser light.

Tip portions of these laser tips are of various shapes, for example, are tapered, planar, curved or the like. A laser tip having an appropriate shape of tip portion may be chosen for the purpose, for example, dissection, hemostasis or the like. Such a laser tip is used as follows, specifically. The laser tip is irradiated with laser light to be heated, and the heated laser tip is put into contact with the dissection target site or the vicinity thereof, so that the blood is coagulated and thus bleeding is stopped.

The tip portion of the laser tip disclosed in Patent Document 1 absorbs the laser light directed from the laser radiation opening. However, a part of the incident laser light may be reflected by the tip portion, and the reflected laser light may be inadvertently directed to a normal tissue, which is not a target of surgery.

PRIOR ART DOCUMENT

Patent Document

Patent Document 1: Japanese Laid-Open Patent Publication No. Hei 6-205789

SUMMARY OF THE INVENTION

Problems to be Solved by the Invention

In light of such a situation, the present invention has an object of providing a laser tip, a laser treatment tool, a laser treatment device and a laser treatment system safely performing a surgery for a laser treatment and, if bleeding occurs, stopping the bleeding.

Means for Solving the Invention

The present invention is directed to a laser tip attachable to a laser radiation opening provided at a tip end of a laser transmission tube, laser light being directed from the laser radiation opening, the laser tip including a mounting portion detachable from the laser radiation opening; a contact portion contactable with a biological tissue, the contact portion being provided to the front of the mounting portion in a direction in which the laser light is directed from the laser radiation opening, with an open space being provided between the contact portion and the mounting portion; a coupler coupling the contact portion and the mounting portion to each other; the contact portion having a reflective portion provided at a rear end thereof, the reflective portion reflecting the laser light, directed forward from the laser radiation opening, toward the coupler.

The present invention is also directed to a laser treatment tool including a laser transmission tube guiding laser light to a surgery target site; and the above-described laser tip.

The present invention is directed to a laser treatment device including a laser oscillator oscillating carbon dioxide gas laser light; a laser transmission tube guiding the laser light oscillated by the laser oscillator to a surgery target site; and the above-described laser tip.

The present invention is directed to a laser treatment system including the above-described laser treatment device; and an endoscope allowing the laser transmission tube to be inserted thereto.

The laser treatment is not limited to any specific laser treatment, and encompasses a laser treatment, such as ESD, using a soft endoscope, a surgical treatment using a hard endoscope, laparotomy, a dental treatment and the like.

The expression "the contact portion being provided to the front of the mounting portion in a direction in which the laser light is directed from the laser radiation opening, with an open space being provided between the contact portion and the mounting portion" indicates that the mounting portion and the contact portion are not coupled with each other so as to close a space but are coupled with each other so as to form an open space, open outside, in a direction perpendicular to the direction in which the laser light is directed.

The reflective portion may have any structure as long as the laser light is reflected toward the coupler. For example, the reflective portion may be flat or concaved. Alternatively, a plurality of the reflective portions may be combined. Still alternatively, a prism or the like may be used to refract the laser light, and the refracted laser light may be reflected toward the coupler.

According to the present invention, a surgery is performed safely for a laser treatment, and bleeding, if occurred, is stopped.

This will be described in more detail. The reflective portion reflects the laser light, directed from the laser radiation opening, toward the coupler. This prevents the reflected laser light from being directed toward a normal tissue, which is not a target of surgery. Thus, the normal biological tissue is prevented from being damaged.

The laser light is directed toward the contact portion. As a result, the contact portion absorbs the energy of the laser light and is heated. The contact portion, thus heated, is put into contact with, for example, the bleeding damaged site, so that the bleeding from the damaged site is stopped.

The coupler couples a part of the contact portion and the mounting portion to each other, with the open space being provided between the contact portion and the mounting portion. The open space is formed between the contact portion and the mounting portion in a direction perpendicular to the direction in which the laser light is directed. With such a structure, for example, a fibrotic tissue, which is difficult to be cut, is held and located in the open space. Thus, the laser light is directed toward the tissue and thus cuts the tissue with certainty.

The contact portion absorbing the laser light is provided to the front of the mounting portion. Thus, the contact portion has a so-called back-stop function of preventing a region to the front of the contact portion from being irradiated with the laser light. Especially, even in the case where a tissue having a thin tissue wall and the vicinity thereof is to be peeled off, the surgery may be performed with no risk of making a perforation.

As can be seen, according to the present invention, the bleeding from the bleeding site is stopped, a normal tissue is prevented from being damaged as a result of being irradiated with the reflected laser light, and perforation is prevented from being made by the laser light. Therefore, the surgery is performed safely.

The laser light does not need to be carbon dioxide gas laser light. The present invention is applicable to a laser treatment using any other type of laser light.

In an embodiment of the present invention, the reflective portion may have a reflective surface making an acute angle with respect to the coupler.

The expression "making an acute angle with respect to the coupler" indicates that the reflective surface and the coupler make an acute angle with respect to each other. The reflective portion having the reflective surface and the coupler do not need to make an acute angle with respect to each other. Namely, a connection portion between the reflective portion and the coupler may have an acute angle or arcked, as long as the reflective surface and the coupler make an acute angle with respect to each other.

According to the present invention, the laser light reflected by the reflective surface (i.e., reflected light) is directed toward the coupler with certainty. Thus, a normal tissue, which is not a target of surgery, is prevented from being irradiated with the reflected light inadvertently. The reflected light is directed toward the coupler holding a laser light absorbing portion. Therefore, the reflected light contributes to the heating of the laser tip, and thus the energy of the laser light is efficiently used.

The reflective surface and the coupler make an acute angle with respect to each other. Therefore, in the state where a biological tissue is held to be located in the open space, the biological tissue is hooked by the recess defined by the reflective surface and the coupler. With such an arrangement, the biological tissue is held certainly, and thus is irradiated with the laser light and is cut with certainty.

A thin blood vessel is cut with certainty. The laser light is directed while the tip of the treatment tool is moved in the left-right direction as seen from the operator, or toward the operator. Therefore, even a tissue that would be otherwise difficult to be cut, for example, a fibrotic tissue or like, is allowed to be easily dissected and peeled off. The tip of the treatment tool is moved toward the operator while the target tissue is held, so that a certain distance is kept from the muscular layer, which is not to be perforated. Therefore, a more precise operation is performed and the safety is high.

In an embodiment of the present invention, the contact portion may have a contact surface at a tip end thereof, the contact surface being curved with a radius of curvature of 10 mm or larger or being flat.

The "curved surface" specifically indicates a protruding curved surface protruding toward the tip end or a recessed curved surface recessed toward the laser radiation opening.

According to the present invention, the bleeding is stopped without enlarging the damaged region.

This will be described in more detail. In the case where, for example, the contact surface has a radius of curvature of +10 mm or larger or is flat, namely, in the case where the contact surface is a protruding curved surface or a flat surface, the contact surface is directly pressed to the damaged site and the laser light is directed toward the contact surface. The contact surface of the contact portion absorbs the energy of the laser light and thus is heated. Therefore, the blood at the damaged site, which is in contact with the contact surface, and in the vicinity of the damaged site is coagulated. Thus, the bleeding from the damaged site is stopped with certainty.

In the case where the contact surface has a radius of curvature of −10 mm or larger, namely, the contact surface is a recessed curved surface, the contact surface is pressed to the damaged site to hold the blood from the damaged site in the recessed portion. The laser light is directed toward the contact portion, so that the blood held in the recessed portion is coagulated by the contact portion heated by the laser light. Thus, the bleeding from the damaged site is stopped.

The action of stopping the bleeding is different in accordance with the radius of curvature of the contact surface. Among the contact portions having contact surfaces that have different radii of curvature or a flat contact surface, an appropriate contact portion may be used in accordance with the site of bleeding or the state of bleeding.

In an embodiment of the present invention, the coupler may be provided with a protrusion protruding toward an optical axis of the laser light directed from the laser radiation opening, the protrusion having a protruding cross-section as seen in a direction of the optical axis.

According to the present invention, the biological tissue held by the contact portion and the coupler so as to be located in the open space is irradiated with laser light with certainty.

This will be described in more detail. In the case where the protrusion is not provided, even if the biological tissue is held by the coupler the contact portion so as to be located in the open space, it is difficult to adjust such that the biological tissue is at a predetermined position to which the laser light is to be directed. In the case where the protrusion protruding toward the optical axis of the laser light is provided, the biological tissue is located on the protrusion.

Thus, the laser light is directed toward the predetermined position in the biological tissue, and the biological tissue is cut at a desired position.

In an embodiment of the present invention, the cross-section of the protrusion may have a triangular shape having an optical axis-side apex of an acute angle.

According to the present invention, the protrusion has a triangular cross-section having an acute angle. Therefore, the protrusion assists the cutting of the biological tissue held in the open space.

In an embodiment of the present invention, a surface of the reflective portion may be coated to decrease a reflectance of the laser light.

According to the present invention, the contact portion absorbs the energy of the laser light to decrease the reflectance of the laser light. Namely, the energy of the laser light that is absorbed by the contact portion is increased. Thus, the contact portion is efficiently heated. In the case where the contact portion is put into contact with a bleeding damaged site in the biological body, the bleeding is stopped with certainty.

In an embodiment of the present invention, the contact portion may be coated to prevent unintentional adhesion with a biological tissue.

The material used to coat the contact surface in order to prevent unintentional adhesion may be any material as long as unintentional adhesion with a biological tissue may be prevented. The coating material may be, for example, titanium carbide (TiC), titanium nitride (TiN), silicon carbide (SiC), silicon nitride, boron nitride (BN) or the like.

According to the present invention, the contact surface in contact with the biological tissue is prevented from being bonded with the biological tissue. This prevents the damaged site or the like from being damaged again when the contact surface is separated from the damaged site after the bleeding from the damaged site is stopped.

The present invention is directed to a laser treatment tool including the laser transmission tube that includes a light guide member guiding the laser light; an outer casing formed of a flat metal plate secured to be integral with the light guide member, the outer casing enclosing an outer circumferential surface of the light guide member; and an attaching portion provided at one end of the light guide member, the laser tip being attachable to the attaching portion;
the outer casing being a cylindrical body having a flexible multi-layer structure and acting as a torque transmitter transmitting a torque at the other end to one end; and also including and a laser tip attached to the attaching portion of the laser transmission tube.

The present invention is directed to a laser treatment device including the above-described laser treatment tool; and a laser oscillator oscillating carbon dioxide gas laser light, the laser oscillator being connected to the other end of the laser transmission tube.

The present invention is directed to a laser treatment system including the above-described laser treatment device; and an endoscope allowing the laser transmission tube to be inserted thereto.

The light guide member may be solid or hollow as long as the light guide member has a transmission efficiency suitable to the laser light to be guided.

The expression secured to be integral refers to a case where a part of the light guide member and a part of the outer casing are secured to each other directly, and also a case where a part of the light guide member and a part of the outer casing are secured to each other indirectly. For example, this expression refers to a case where a fixing member fixing the light guide member and the outer casing to each other; a case where one point of a plurality of points in the outer casing, among a tip end, a base end, a center portion and the like of the outer casing, and the light guide member are secured to each other;
and a case where a fixing member fixing the light guide member and a tip portion or the like of the outer casing are secured to each other directly or indirectly.

The "torque transmitter" refers to a cylindrical body formed of a metal plate wound around such that a multi-layer structure is formed and such that an inner layer and an outer layer overlap each other. The "torque transmitter" encompasses a body in which the layers are wound in the same direction, and a body in which the layers are wound in different directions.

The metal plates of the layers may be the same as each other or different from each other. The winding pitches of the layers may be the same as each other or different from each other.

According to the present invention, the diameter of the laser transmission tube is decreased.

This will be described in more detail. For example, the ESD which is minimally invasive medical practices are performed by use of a treatment device using a laser light.

As disclosed in, for example, Patent Document 2 (Japanese Laid-Open Patent Publication No. 2004-321463), a generally used laser treatment device using laser light includes a laser transmission tube that is provided around an outer circumferential surface of a flexible fiber and is covered with an outer casing in bellows. With such a structure, the fiber guiding the laser light is oriented in a desired direction to direct the laser light. Even if the fiber is broken, the outer casing prevents the laser light from leaking outside.

However, in the laser transmission tube disclosed in Patent Document 2, the outer casing in bellows covers the outer circumferential surface of the fiber. This inevitably increases the outer diameter of the laser transmission tube. The laser transmission tube is not insertable into the device insertion opening of the endoscope. Especially because the diameter of the endoscope is now being decreased in order to decrease the load on the patients, it is an important problem to decrease the diameter of the laser transmission tube.

According to the present invention, as described above, the outer casing having a multi-layer structure is formed of a flat metal plate and encloses the outer circumferential surface of the light guide member. With such an arrangement, the outer diameter of the outer casing, which corresponds to the thickness of the metal plate, is the outer diameter of the laser transmission tube. Thus, the outer diameter of the laser transmission tube is decreased.

In addition, the outer casing enclosing the outer circumferential surface of the light guide member is formed of a metal plate and has a multi-layer structure. Therefore, even if the light guide member is damaged, the laser light, if leaking from the damaged part, is blocked by the outer casing and is prevented from leaking out of the laser transmission tube.

The outer casing is secured to be integral with the light guide member. Therefore, the rotation of the other end (rear end) of the outer casing is transmitted to one end (tip end) of the light guide member. This allows the one end of the light guide member to be rotated by a desired amount. The position of the one end (tip end) of the light guide member is fine-tuned in a circumferential direction.

With the above-described arrangement, in the case where, for example, assist gas is sprayed from the tip end of the laser transmission tube or the laser tip is attached, the other end, which is the base end, is rotated. The outer casing acting as the torque transmitter transmits the rotation to cause the tip end to rotate in accordance with the rotation of the base end. Thus, the position of the spray opening of the assist gas or the orientation of the laser tip is fine-tuned in the circumferential direction and determined. Therefore, the assist gas is sprayed from a desired position, or the laser tip is located in a desired orientation.

In an embodiment of the present invention, the outer casing may include a first layer spirally wound around the outer circumferential surface of the light guide member; and a second layer spirally wound around an outer circumferential surface of the first layer in a direction opposite to the first layer.

For example, flat metal plates forming the first layer and the second layer may be located side by side with a predetermined coil gap, may form a planar surface in the longitudinal direction, or may overlap in the longitudinal direction such that a rear portion of one of the layers and a front portion of the other layer overlap each other. The first layer and the second layer do not need to have the same structure.

According to the present invention, the torque generated by the rotation of the rear end of the laser transmission tube is transmitted to the tip end certainly.

When, for example, the laser transmission tube is rotated at the rear end thereof in a forward direction, in which the first layer is wound, the first layer is tightened to the light guide member. Therefore, the torque in the forward direction is transmitted to the tip end of the laser transmission tube. By contrast, when the laser transmission tube is rotated at the rear end thereof in a direction opposite to the direction in which the first layer is wound, the first layer is loosened from the light guide member. However, the second layer is tightened to the light guide member. Therefore, the torque in the reverse direction is transmitted to the tip end of the laser transmission tube.

In this manner, the torque of the rotation at the rear end of the laser transmission tube is transmitted to the tip end with certainty.

In an embodiment of the present invention, an outer circumferential surface of the outer casing may be enclosed by an outer layer protective member formed of a waterproof resin.

The "outer layer protective member" encompasses, for example, a resin outer casing protective tube, a resin coat, a thermally shrinkable tube and the like.

According to the present invention, the laser transmission tube is smoothly inserted into the device insertion path formed in the endoscope, and the device insertion path is prevented from being damaged.

This will be described in more detail. The outer casing is enclosed by the resin outer layer protective member. This prevents the outer casing from expanding. In addition, the outer layer protective member, which is provided between the outer casing formed of a metal material and the device insertion path, prevents the outer casing from being stuck with the laser transmission tube. This allows the laser transmission tube to be smoothly inserted into the device insertion path, and prevents the outer casing from damaging the device insertion path.

The outer layer protective member, which is waterproof, prevents a liquid such as a saline solution, a washing liquid a bodily fluid or the like from entering from the outside of the outer casing. Thus, a region inner to the outer casing is protected from being corroded or contaminated with such a liquid.

The outer layer protective member encloses the outer circumferential surface of the outer casing. Therefore, the cooling medium is prevented from leaking from a region inner to the outer casing to the outside. Even if the light guide member is damaged, the outer layer protective member suppresses the outer casing from being deformed and prevents the laser light from leaking outside because the energy of the laser light leaking from the laser transmission tube is absorbed by the cooling medium flowing in the cooling path.

In an embodiment of the present invention, the outer layer protective member may be formed of a thermally shrinkable tube.

According to the present invention, the outer casing is easily enclosed by the outer layer protective member, and the outer layer protective member is made thin. This allows the outer diameter of the laser transmission tube to be decreased, while the waterproofness is provided.

In an embodiment of the present invention, a cooling path allowing a cooling medium to flow therein along the light guide member may be provided between the light guide member and the outer casing.

The cooling medium encompasses distilled water, tap water, gas such as air, nitrogen gas or the like, and a gel-like substance.

According to the present invention, the light guide member heated by the laser light is cooled by the cooling medium flowing in the cooling path. This improves the durability of the laser transmission tube treating the surgery target site with the laser light with certainty.

In an embodiment of the present invention, the cooling path may include a first cooling path and a second cooling path formed along the light guide member, and the cooling path may further include a coupling path communicating the first cooling path and the second cooling path to each other, the coupling path being provided at one end.

According to the present invention, the cooling medium which has flown in one of the first cooling path and the second cooling path is allowed to flow to the other of the first cooling path and the second cooling path via the coupling path. In this manner, the cooling medium is recovered. The cooling medium is circulated, and the light guide member heated by the laser light is efficiently cooled. The cooling medium is circulated in the first cooling path or the second cooling path without leaking to the surgery target site.

Effect of the Invention

The present invention provides a laser tip, a laser treatment tool, a laser treatment device and a laser treatment system safely performing a surgery for a laser treatment safely and, if bleeding occurs, stopping the bleeding.

DESCRIPTION OF THE PREFERRED EMBODIMENTS

Hereinafter, an embodiment according to the present invention will be described with reference to the drawings.

Figure 1:
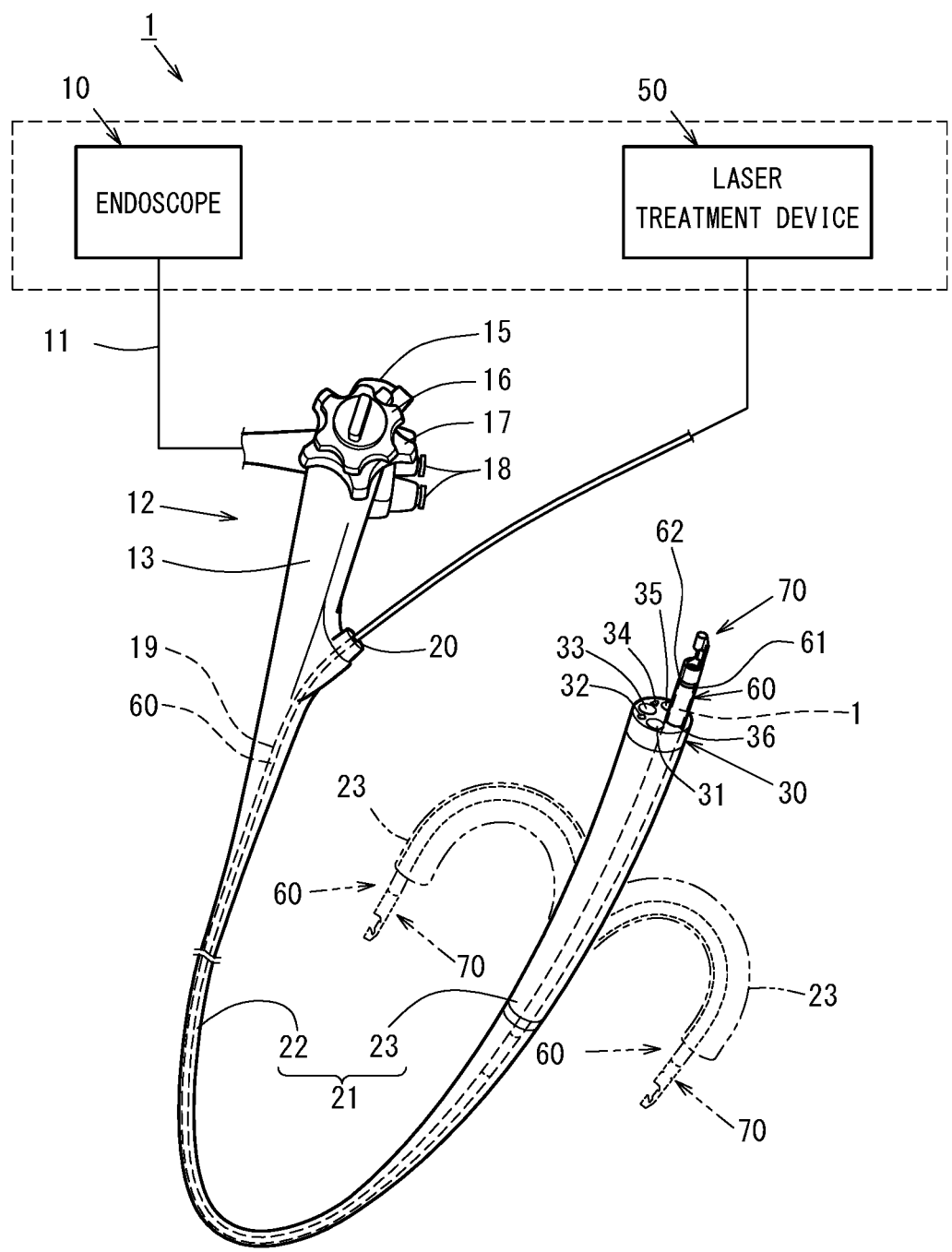
FIG. 1 is a schematic structural view of a laser treatment system including an endoscope device and a laser treatment device in an embodiment.
Figure 2:
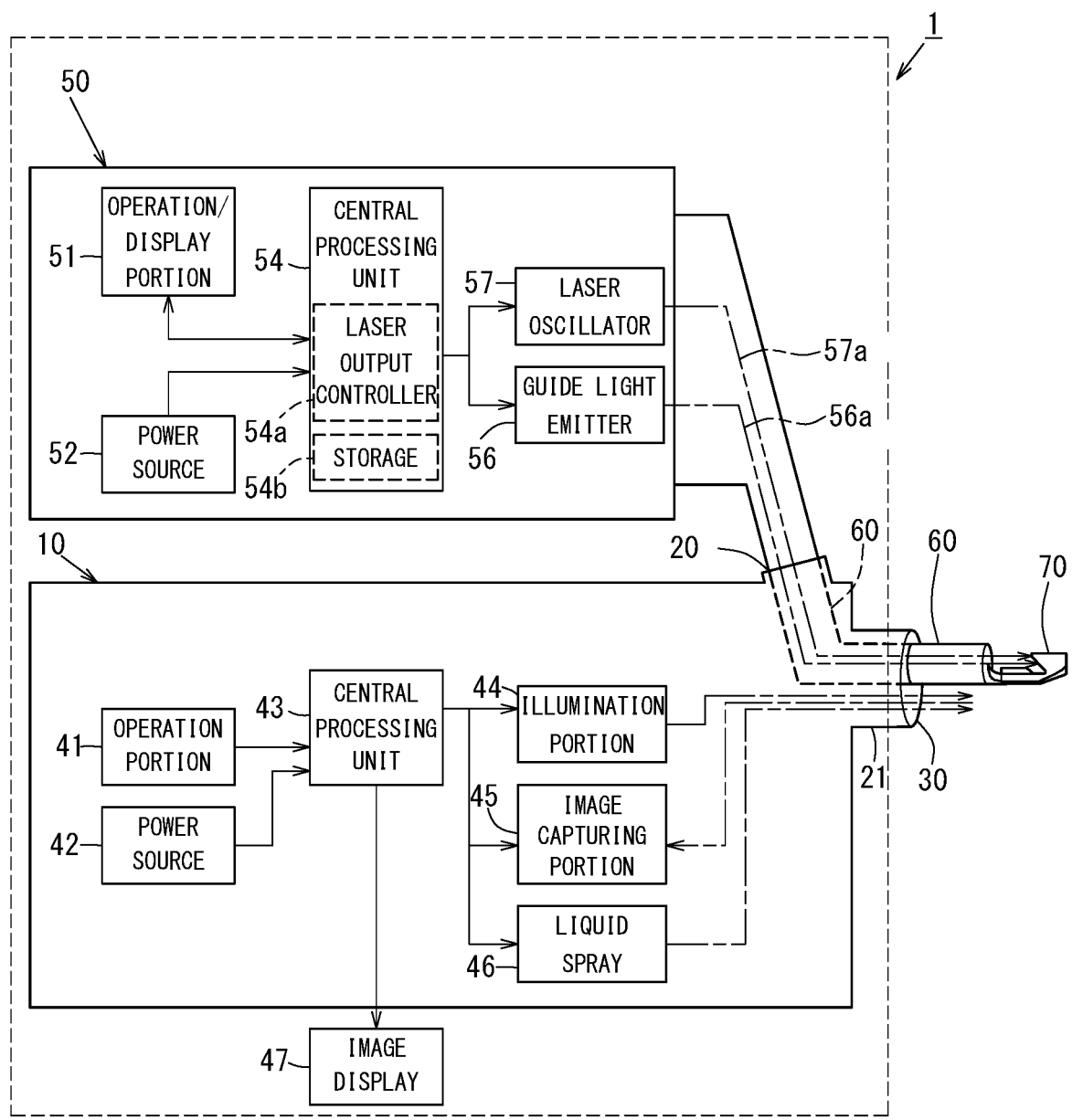
FIG. 2 is a block diagram showing a structure of the endoscope device and the laser treatment device.

FIG. 1 is a structural view schematically showing a structure of a laser treatment system 1 including an endoscope device 10 and a laser treatment device 50. FIG. 2 is a block diagram showing a structure of the endoscope device 10 and the laser treatment device 50.

As shown in FIG. 1, the endoscope device 10 includes a device main body and an operation unit 12 connected with the device main body via a connection cable 11.

The operation unit 12 mainly includes an operation portion 13 and an endoscope tube 21.

The operation portion 13 includes an eye contact portion 15, a top/bottom angle knob 16, a left/right angle knob 17, an operation button 18, a device insertion opening 20, and the like.

The operation button 18 receives an operation input such as air transmission, liquid transmission, absorption, zooming or the like.

The endoscope tube 21 includes a flexible tube portion 22, a curved tube portion 23, and a tip portion 30 provided in this order from a base end (rear end) to a tip end thereof. The endoscope tube 21 has a device insertion path 19 formed therein. The device insertion path 19 is continuous from the device insertion opening 20 to a device outlet 36 of the tip portion 30. The device insertion path 19 acts as a treatment device insertion path through which a treatment device such as a forceps, a laser transmission tube 60 or the like is insertable.

In FIG. 1, the laser treatment system 1 is shown as having a diameter increasing from the middle of the flexible tube 22 to a tip end of the curved tube 23. The laser treatment system 1 is shown in this way merely to make the structure thereof easy to understand. In actuality, the endoscope tube 21 has a constant diameter that is suitable for the endoscope tube 21 to be inserted into a biological organ such as esophagus, stomach, intestine or the like.

The flexible tube 22 has a cylindrical shape that is appropriately curved. An appropriate treatment device such as a forceps of the like may be inserted from the device insertion opening 20 to the tip portion 30. In this embodiment, the laser transmission tube 60 is inserted as the treatment device into the flexible tube 22 in the state where a laser tip 70 of a laser treatment device 50 is attached to a tip end of the laser transmission tube 60.

The curved tube 23 may be curved in an up-down direction by an operation made on the top/bottom angle knob 16, and may be curved in a left-right direction by an operation made on the left/right angle knob 17.

The tip portion 30 includes light guides 31 and 35, a sub liquid transmission opening 32, a lens 33, a nozzle 34, and the device outlet 36.

The light guides 31 and 35 are illumination portions providing illumination light for image capturing. The light guides 31 and 35 illuminate the inside of the body to which light would not reach otherwise, so that the inside of the body is observed and operated on.

Through the sub liquid transmission opening 32, a liquid such as a dye liquid or the like is released.

The lens 33 includes a lens collecting the illumination light provided by the light guides 31 and 35 or the like to acquire a captured image, and an image capturing element located to the rear of the lens.

The nozzle 34 is a portion releasing a washing liquid or the like, usable to wash the lens 33, toward the lens 33.

The device outlet 36 is an outlet of the treatment device such as, for example, the laser transmission tube 60 attached to the laser treatment device 50. The laser transmission tube 60 is longer than a device insertion path length, which is the entire length of the endoscope tube 21. The laser transmission tube 60 will be described in detail below.

As shown in FIG. 2, the laser treatment device 50 includes an operation/display portion 51, a power source 52, a central processing unit 54, a guide light emitter 56, and a laser oscillator 57.

The operation/display portion 51 receives an operation input such as a laser output setting, an operation mode change or the like, transmits such an input signal to the central processing unit 54, receives a display signal on laser output conditions, a device operation state or the like from the central processing unit 54, and displays appropriate information.

The power source 52 supplies the power for operations to components such as the central processing unit 54 and the like.

The central processing unit 54 executes various control operations on the components. The central processing unit 54 includes a laser output controller 54a and a storage 54b.

The laser output controller 54a controls an output value of laser light 57a to be provided by the laser oscillator 57 in accordance with the output or the operation mode set by the operation/display portion 51. The storage 54b has, stored thereon, control data such as the output setting, the operation mode setting and the like and also appropriate data.

The guide light emitter 56 emits guide light 56a to indicate the position to which the laser light 57a for treatment is to be directed. With the guide light 56a, the position to which the laser light 57a for treatment is to be directed is checked.

The laser oscillator 57 oscillates the laser light 57a usable for a surgery. In this embodiment, the laser light 57a is carbon dioxide gas laser light. An operation such as setting of the radiation strength of the carbon dioxide gas laser light, start/stop of the radiation or the like is performed by a manual operation on the operation/display portion 51 and by a control output provided by the central processing unit 54. A part of, or the entirety of, the manual operation may be replaced with a stomping operation made by use of a foot controller (not shown) that is communicable with the laser treatment device 50 to control the laser treatment device 50.

The guide light 56a provided by the guide light emitter 56 and the laser light 57a oscillated by the laser oscillator 57 are both transmitted by one laser transmission tube 60.

The endoscope device 10 includes an operation portion 41, a power source 42, a central processing unit 43, an illumination portion 44, an image capturing portion 45, a liquid spray 46, and an image display 47.

The operation portion 41 transmits an operation input provided by the operation portion 13 (see FIG. 1) to the central processing unit 43. Namely, the operation portion 41 transmits an operation of curving the curved tube 23 made by an operation on the top/bottom angle knob 16 or the left/right angle knob 17, an operation of pressing the operation button 18 or the like. Alternatively, separately from the operation unit 12, another operation portion may be provided in, for example, a controller main body (not shown) of the endoscope device 10, so that an operation of setting an amount of illumination light, capturing and storing a still image, or the like is transmitted to the central processing unit 43.

The power source 42 supplies power for operations to components such as the central processing unit 43 and the like. The central processing unit 43 executes various control operations on the components.

The illumination portion 44 provides the illumination light from the light guides 31 and 35 (see FIG. 1).

The image capturing portion 45 captures an image, transmitted from the lens 33 and the image capturing element (see FIG. 1) located to the rear of the lens 33, to provide a captured image necessary for the surgery, or to perform image processing. Such captured images are provided continuously in real time, so that the operator performs surgery smoothly.

The liquid spray 46 sprays the liquid from the sub liquid transmission opening 32. The liquid spray 46 also sprays the liquid from the nozzle 34. The image capturing portion 45 may be provided in the vicinity of the tip portion 30, or in the controller main body (not shown) of the endoscope device 10.

The image display 47 displays an image in accordance with a signal transmitted from the central processing unit 43. The image encompasses the captured image captured by the image capturing portion 45. Therefore, the operator may perform the surgery while checking the captured images displayed on the image display 47 in real time.

Now, with reference to FIG. 3 through FIG. 5, a structure of the laser transmission tube 60 and a structure of the laser tip 70 attachable to the tip end of the laser transmission tube 60 will be described.

Figure 3:
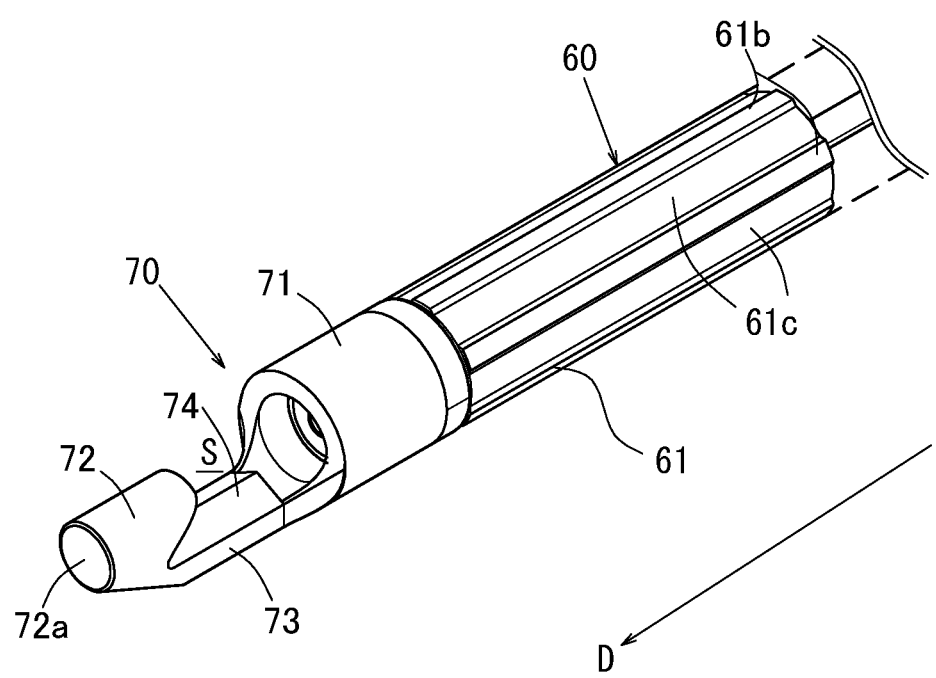
FIG. 3 is a schematic perspective view of a laser tip attached to a tip end of a hollow waveguide tube.

FIG. 3 is an enlarged perspective view of the tip end of the laser transmission tube 60, more specifically, is a schematic perspective view of the laser tip 70 attached to the tip end of the laser transmission tube 60. FIG. 4 is a schematic exploded perspective view of the laser transmission tube 60 and the laser tip 70. FIG. 5A to FIG. 5C illustrate the laser tip 70 attached to the laser transmission tube 60. In FIG. 3 and FIG. 4, a laser tube 61 included in the laser transmission tube 60 is partially represented by the dashed line to indicate that a component provided inside the laser tube 61 is shown.

FIG. 5A to FIG. 5C will be described in more detail. FIG. 5A is a side view of the laser transmission tube 60 having the laser tip 70 attached thereto. FIG. 5B is a cross-sectional view taken along line A-A in FIG. 4, namely, a longitudinal cross-sectional view of a state where the laser tip 70 is detached from the laser transmission tube 60. FIG. 5C is a cross-sectional view taken along line B-B in FIG. 5A.

Figure 4:
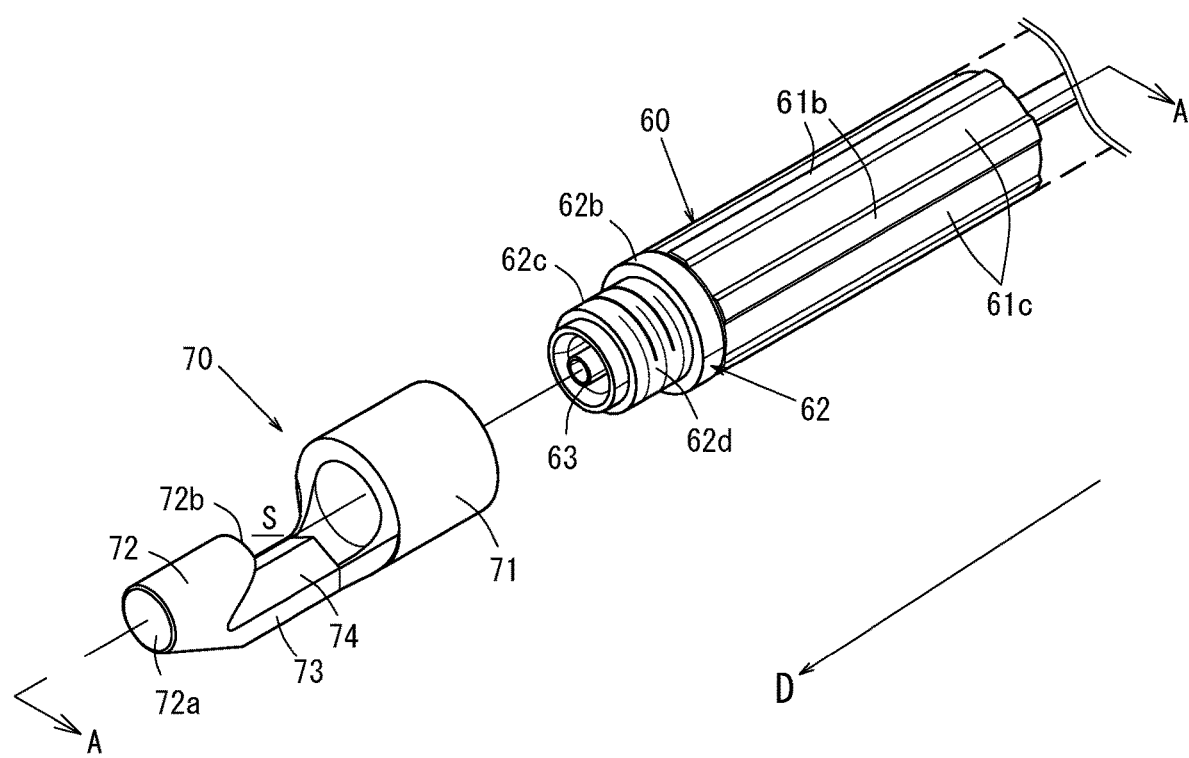
FIG. 4 is a schematic exploded perspective view of the tip end of the hollow waveguide tube and the laser tip.
Figure 5A:
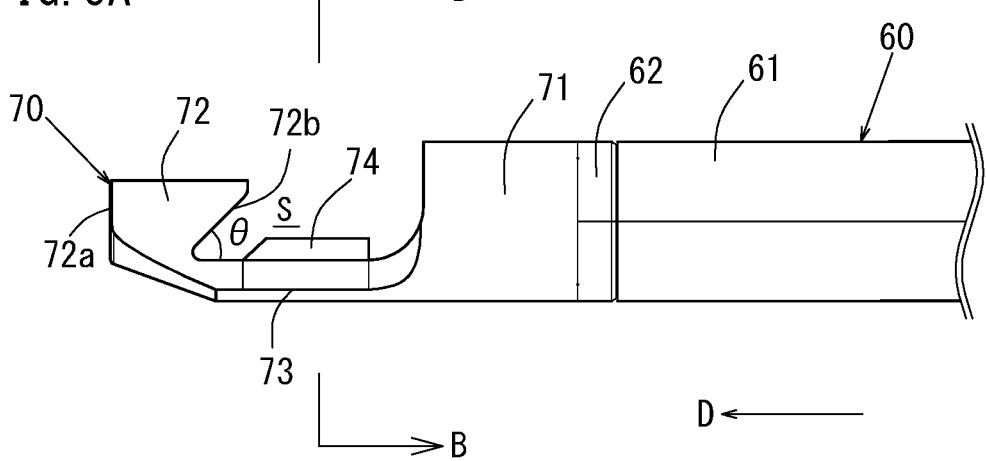
FIGS. 5A to 5C illustrate the laser tip attached to the hollow waveguide tube.
Figure 5B:
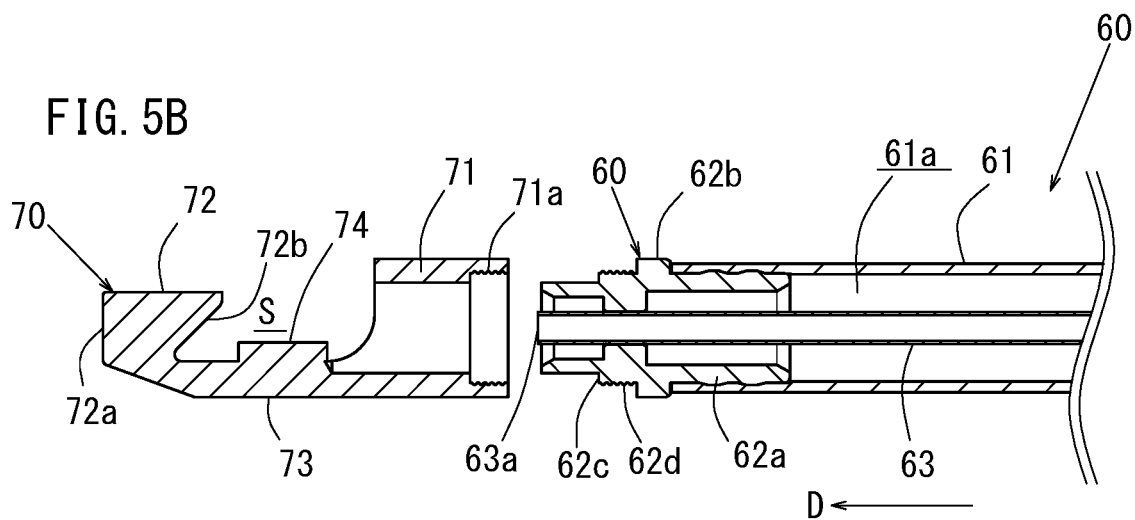
Figure 5C:
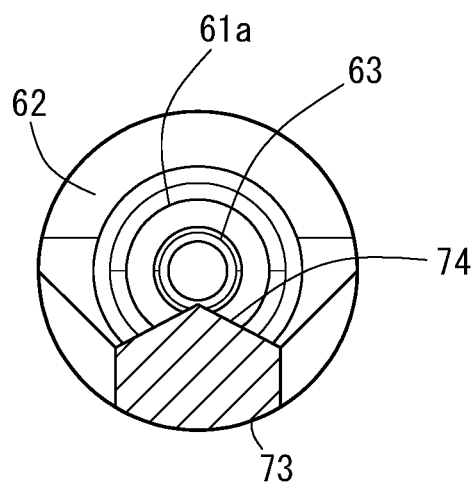

As shown in FIG. 3 and FIG. 4, the laser transmission tube 60 includes the laser tube 61, a laser tip-side attaching portion 62 provided at a tip end of the laser tube 61, and a hollow waveguide tube 63 inserted into the laser tube 61. As described above, the laser transmission tube 60 is longer than the endoscope tube 21.

The laser tube 61 is a hollow and flexible resin tube having an insertion space 61a (see FIG. 5B) formed therein, through which the hollow waveguide tube 63 is insertable. As shown in FIG. 3 and FIG. 4, the laser tube 61 includes a plurality of outer protruding portions 61b and a plurality of outer recessed portions 61c formed in an outer circumferential surface thereof. The outer protruding portions 61b each have an outer diameter that is slightly smaller than an inner diameter of the device insertion path 19 of the endoscope tube 21. The outer recessed portions 61c are each provided between adjacent outer protruding portions 61b. The outer protruding portions 61b and the outer recessed portions 61c are provided alternately in a circumferential direction. As seen in an optical axis direction D corresponding to a direction in which the laser light 57a is directed, a cross-section of the laser tube 61 is generally gear-like with the outer protruding portions 61b and the outer recessed portions 61c.

In the state where the laser tube 61 having the above-described structure is inserted into the device insertion path 19, the outer protruding portions 61b contact, and is firmly secured to, the device insertion path 19, and the laser tube 61 is flexibly bendable in accordance with the endoscope tube 21 being bent.

As shown in FIG. 4 and FIG. 5B, the laser tip-side attaching portion 62 includes a transmission tube-side attaching portion 62a, a tube coupler 62b, and a laser tip attaching portion 62c, which are provided in this order from a rear end of the laser tip-side attaching portion 62.

As shown in FIG. 5B, the transmission tube-side attaching portion 62a has a cylindrical shape having an outer diameter that is approximately equal to an inner diameter of the laser tube 61 and also having an inner diameter that is slightly larger than an outer diameter of the hollow waveguide tube 63 described below. The transmission tube-side attaching portion 62a allows the hollow waveguide tube 63 to be inserted thereto. The transmission tube-side attaching portion 62a is inserted into the insertion space 61a, so that the laser tip-side attaching portion 62 is fit to the laser tube 61.

The tube coupler 62b is a cylindrical body attached to a tip end of the transmission tube-side attaching portion 62a, and has an outer diameter that is slightly smaller than the inner diameter of the device insertion path 19 and has an inner diameter that is approximately equal to the outer diameter of the hollow waveguide tube 63. In the state where the laser tip-side attaching portion 62 is attached to the laser tube 61, the outer circumferential surface of the laser tube 61 and an outer circumferential surface of the laser tip-side attaching portion 62 are flush with each other, and a laser radiation opening 63a described below is secured to a central part of the laser tube 61.

The laser tip attaching portion 62c is a cylindrical body extending forward from a tip end of the tube coupler 62b, and has an outer diameter that is approximately equal to the outer diameter of the transmission tube-side attaching portion 62a. The laser tip attaching portion 62c has a thread 62d, extending in the optical axis direction D, in an outer circumferential surface thereof.

The hollow waveguide tube 63, which is insertable into the insertion space 61a, is a hollow cylindrical body, and an inner circumferential surface thereof is entirely covered with a dielectric thin film (not shown). The hollow waveguide tube 63 includes the laser radiation opening 63a provided at a tip end thereof. The laser light 57a is directed from the laser radiation opening 63a.

The cylindrical body forming the hollow waveguide tube 63 is lengthy and is formed of a material, such as glass or the like, that has a smooth surface and is suitable to be covered with a reflective film of silver or the like and a dielectric thin film. The dielectric thin film is formed of an appropriate material that efficiently reflects laser light such as COP (cyclic olefin polymer), polyimide or the like.

As described above, the inner circumferential surface of the hollow waveguide tube 63 is covered with a reflective film of silver or the like and a dielectric thin film. Therefore, the laser light 57a is propagated in the hollow waveguide tube 63 at a high transmission efficiency.

The laser tip 70 attachable to the laser transmission tube 60 is formed of stainless steel. As shown in FIG. 3 through FIG. 5, the laser tip 70 includes a laser transmission tube attaching portion 71 detachable from the laser transmission tube 60, a contact portion 72 located to the front of, and a predetermined distance away from, the laser transmission tube attaching portion 71, and a coupler 73 coupling the laser transmission tube attaching portion 71 and the contact portion 72 to each other. The laser transmission tube attaching portion 71, the contact portion 72 and the coupler 73 are integrally formed with each other.

The laser transmission tube attaching portion 71 corresponding to an "attaching portion" is a cylindrical body having an outer diameter that is approximately equal to the outer diameter of the tube coupler 62b and an inner diameter that is approximately equal to the outer diameter of the laser tip attaching portion 62c. The laser transmission tube attaching portion 71 has a thread 71a, engageable with the thread 62b, in an inner circumferential surface of a rear portion thereof (see FIG. 5B).

The contact portion 72 provided at a tip end of the laser tip 70 has an outer diameter that is approximately equal to an inner diameter of the laser tip attaching portion 62c. Namely, the contact portion 72 is a generally cylindrical solid body slightly smaller than the laser transmission tube attaching portion 71. The contact portion 72 has, at a tip end thereof, a contact surface 72a contactable with a biological tissue, and also has, at a rear end thereof, a reflective surface 72b reflecting the laser light 57a directed from the laser radiation opening 63a (see FIG. &A).

The contact surface 72a is a circular flat surface extending along a cross-section perpendicular to the optical axis direction D, and is formed such that the laser light 57a is directed toward a position corresponding to the center of the circular shape thereof. The contact surface 72a is coated with titanium carbide (TiC) in order to prevent unintentional adhesion with a biological tissue.

The reflective surface 72b is provided at a surface of the contact portion 72 that faces the laser radiation opening 63a. As shown in FIG. 5A, the reflective surface 72b is provided to make an acute angle with respect to the optical axis direction D so as to face the coupler 73 described below. The reflective surface 72b is coated with a coating portion that decreases a reflectance of the laser light 57a. In other words, the reflective surface 72b is coated with a coating portion that absorbs the energy of the laser light 57a.

As shown in FIG. 3 through FIG. 5, the coupler 73, coupling the laser transmission tube attaching portion 71 and the contact portion 72 located to be away from each other by a predetermined distance, couples a bottom part of the laser transmission tube attaching portion 71 and a bottom part of the contact portion 72 to each other along the optical axis direction D. The coupler 73 and the reflective surface 72b are designed so as to make an angle θ of 45 degrees.

In this embodiment, the angle made by the coupler 73 and the reflective surface 72b is 45 degrees. The angle is not limited to 45 degrees. The coupler 73 and the reflective surface 72b may make any acute angle.

On a top surface of an inner portion of the coupler 73, a protrusion 74 protruding toward an optical axis of the laser light 57a is formed. As shown in FIG. 5C, the protrusion 74 has a triangular cross-section having an optical axis-side apex of an acute angle as seen in the optical axis direction D.

The laser transmission tube attaching portion 71 of the laser tip 70 having the above-described structure is engaged with the laser tip attaching portion 62c, so that the laser tip 70 is attached to the laser transmission tube 60. The laser treatment device 50 is operated in this state to oscillate the laser light 57a, so that the laser light 57a is directed toward the contact portion 72.

In the state where the laser tip 70 is attached to the laser transmission tube 60, the laser light 57a is directed. In this case, a bleeding site E stops bleeding and a biological tissue is cut by use of the laser tip 70. With reference to FIG. 6A, FIG. 6B, FIG. 7A and FIG. 7B the bleeding from the bleeding site E is stopped and the biological tissue is cut by use of the laser tip 70 will be described.

Figure 6A:
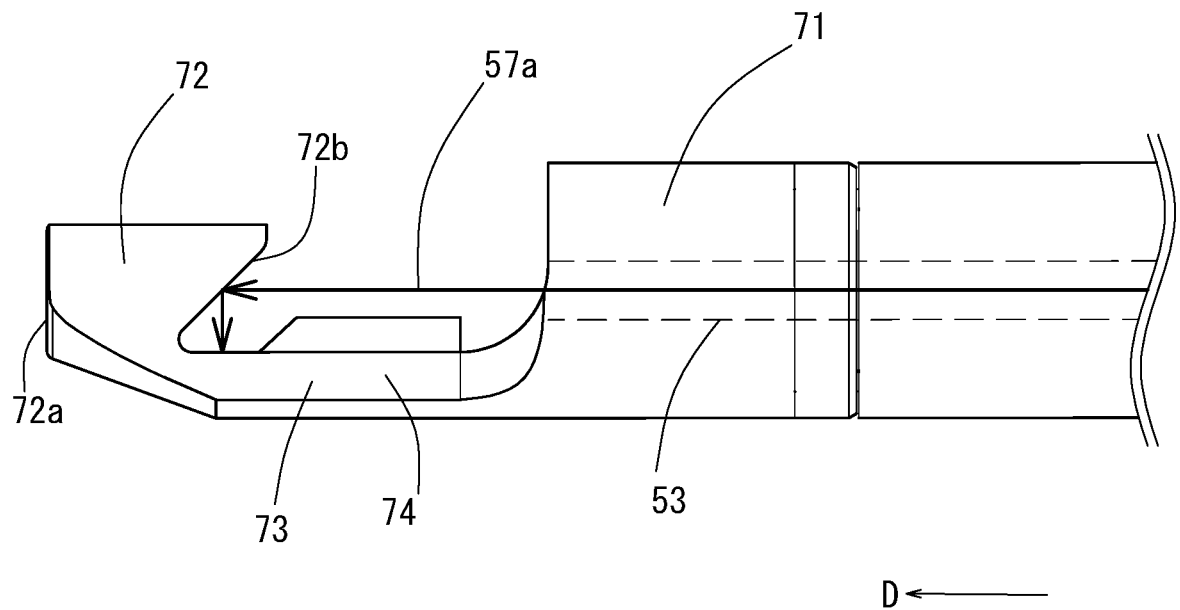
FIGS. 6A and 6B illustrate hemostasis performed by use of the laser treatment system.
Figure 6B:
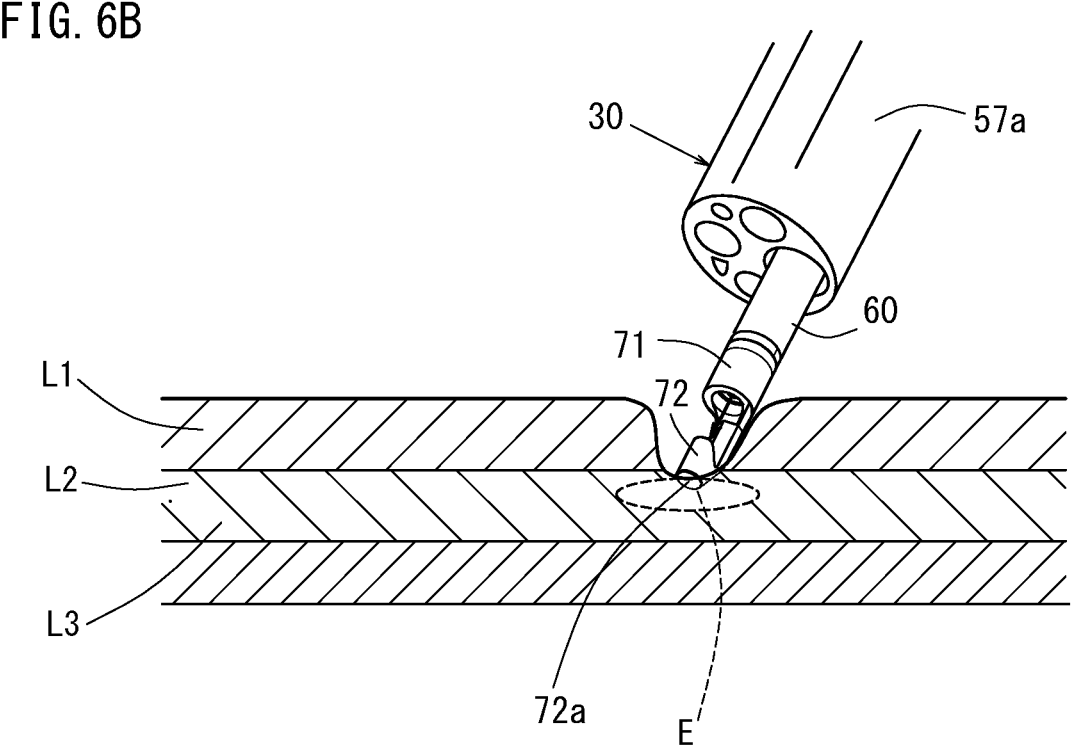

FIG. 6A is a side view showing an optical path of the laser light 57a directed in the state where the laser tip 70 is attached to the laser transmission tube 60. FIG. 6B illustrates a state where the contact surface 72a is pressed to the bleeding site E.

As shown in FIG. 6A, in the state where the laser tip 70 is attached to the laser transmission tube 60, the laser light 57a directed from the laser radiation opening 63a is reflected by the reflective surface 72b toward the coupler 73.

Since the reflective surface 72b is coated with the coating portion absorbing the energy of the laser light 57a, the contact portion 72 irradiated with the laser light 57a is efficiently heated. As shown in FIG. 6B, the contact surface 72*a* of the heated contact portion 72 is put into contact with the bleeding site E, so that blood B is efficiently coagulated.

Since the reflective surface 72*b* is coated with the coating portion absorbing the energy of the laser light 57*a*, the energy of the laser light 57*a* reflected toward the coupler 73 is decreased. Therefore, even if such reflected laser light 57*a* directed toward the coupler 73 is further reflected and diffused, a normal biological tissue is not damaged.

As shown in FIG. 3 through FIG. 5, the coupler 73 couples a part of the laser transmission tube attaching portion 71 and a part of the contact portion 72 located away from each other by a predetermined distance. Therefore, atop part of the coupler 73 does not couple the laser transmission tube attaching portion 71 and the contact portion 72. An open space S communicated with the outside is formed between the laser transmission tube attaching portion 71 and the contact portion 72.

Figure 7A:
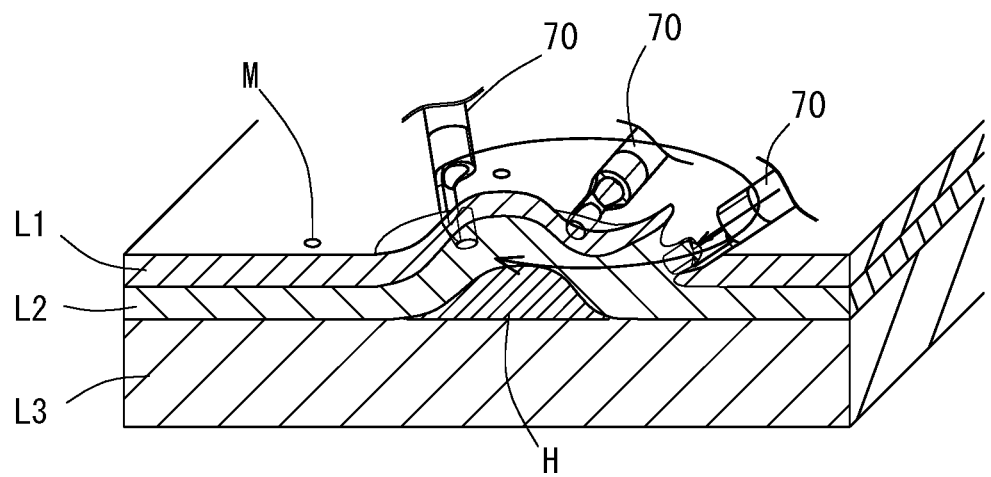
FIGS. 7 A and 7B illustrate cutting of a biological tissue by use of the laser tip.
Figure 7B:
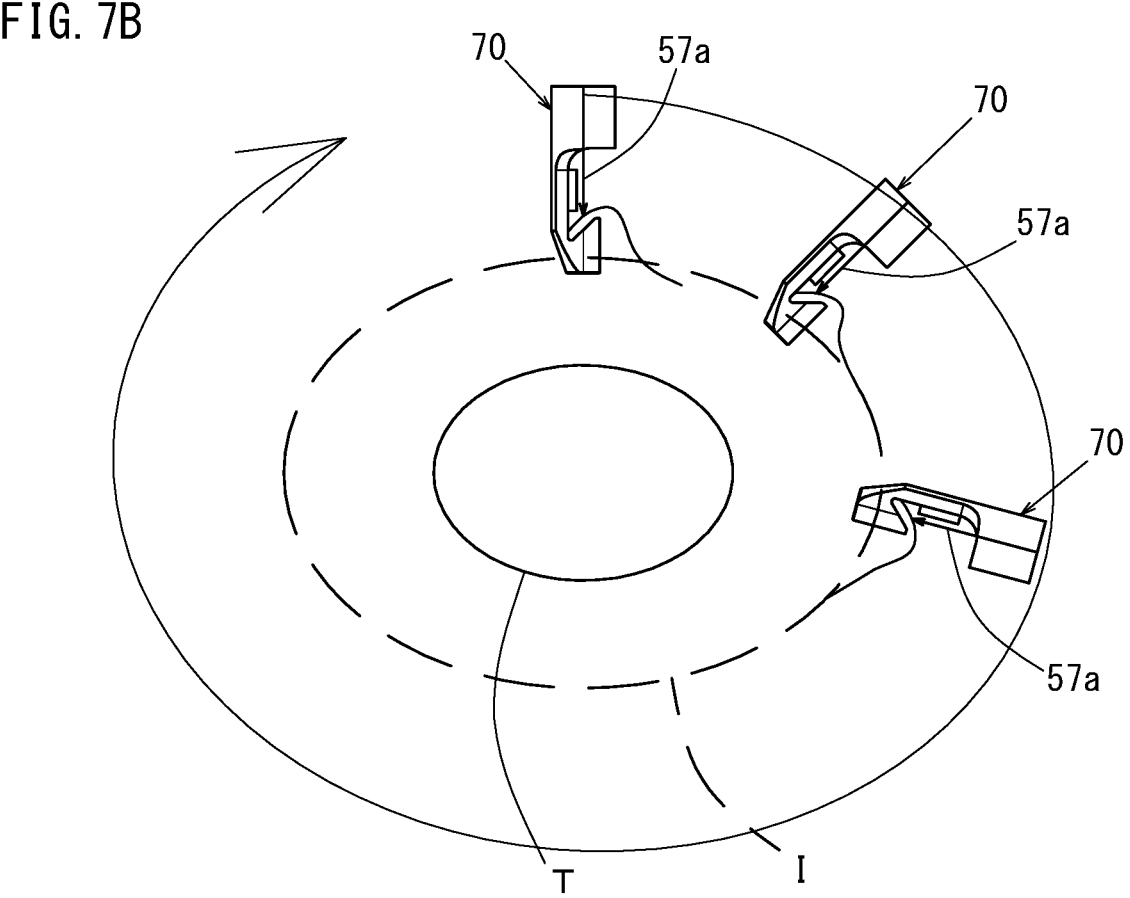

With reference to FIG. 7A and FIG. 7B, a method by which a biological tissue, more specifically, a tissue of submucosa L2 in the vicinity of an affected tissue T to be peeled off is located in the open space S and cut will be described.

FIG. 7A and FIG. 7B illustrate how the submucosa L2 is cut by use of the laser tip 70. In more detail, FIG. 7A is a schematic perspective view showing how the submucosa L2 is cut by use of the laser tip 70. FIG. 7B is a schematic plan view of FIG. 7A.

The affected tissue T, which is a target of peeling, is in a mucosal layer L1. First, the laser light 57*a* is directed to a plurality of positions enclosing the affected tissue T to mark a range to be cut off (marking M). Next, hyaluronic acid H is injected into the submucosa L2 below the affected tissue T to pull up the affected tissue T. The laser light 57*a* is directed along the affected tissue T to dissect the mucosal layer L1. Hereinafter, the line along which the mucosal layer L1 is dissected by the radiation of the laser light 57*a* will be referred to as a "dissection line I".

In this state, the mucosal layer L1 is dissected along the dissection line I, but a portion of the mucosal layer L1 inner to the dissection line I (portion closer to the affected tissue T) is continuous to the submucosa L2.

Next, the laser transmission tube 60 is pulled out from the device insertion opening 20, the laser tip 70 is attached to the tip end of the laser transmission tube 60, and then the laser transmission tube 60 is inserted again into the device insertion opening 20. As shown in FIG. 7A and FIG. 7B, the contact portion 72 is inserted along the dissection line I, the reflective surface 72*b* is caused to hook and pull out the tissue of the submucosa L2 continuous to the portion of the mucosal layer L1 inner to the dissection line I, and the laser light 57*a* is directed in the state where the tissue of the submucosa L2 is tensioned. As a result, the tissue of the submucosa L2 irradiated with the laser light 57*a* is cut.

The laser tip 70 is moved along the dissection line I as if mowing the submucosa L2, and the tissue of the submucosa L2 is hooked and pulled out similarly. The laser light 57*a* is directed in the state where the tissue of the submucosa L2 is tensioned. In this manner, the tissue of the submucosa L2 is cut while the laser tip 70 is moved along the dissection line I. Thus, the affected tissue T is cut away from the submucosa L2 around the affected tissue T. As a result, the affected tissue T is separated.

In this step, the laser light 57*a* from the laser radiation opening 63*a* is directed toward the reflective surface 72*b*. Therefore, the submucosa L2 or a muscular layer L3 is not inadvertently irradiated with the laser light 57*a*, and the muscular layer L3 is prevented from being perforated.

Since the protrusion 74 is provided, the tissue of the submucosa L2 is allowed to be located at a position to which the laser light 57*a* is directed. Thus, the tissue of the submucosa L2 is cut with certainty. Since the protrusion 74 has a triangular cross-section having the optical axis-side apex of an acute angle, the tissue of the submucosa L2 is more easily cut while being tensioned.

In the above-described example, the contact surface 72*a* is flat. The contact surface does not need to be flat. The contact surface may be mildly protruding or recessed.

Hereinafter, with reference to FIG. 8A, FIG. 8B, FIG. 9 A and FIG. 9B, a laser tip 70*x* having a mildly protruding contact surface and a laser tip 70*y* having a mildly recessed contact surface will be described. Among the components of the laser tip 70*x* and the laser tip 70*y*, the same components as those of the laser tip 70 will bear the same reference signs, and descriptions thereof will be omitted.

Figure 8A:
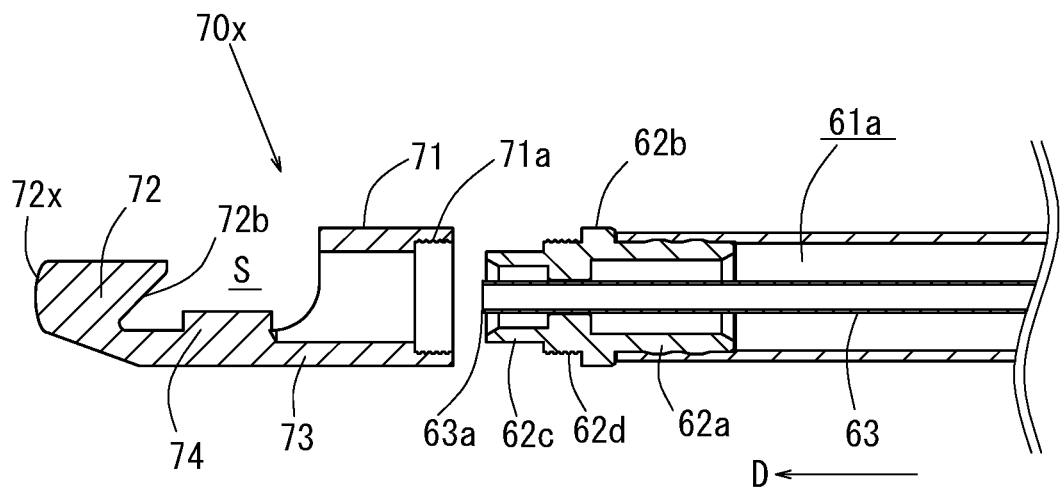
FIGS. 8 A and 8B illustrate a laser tip in another embodiment.
Figure 8B:
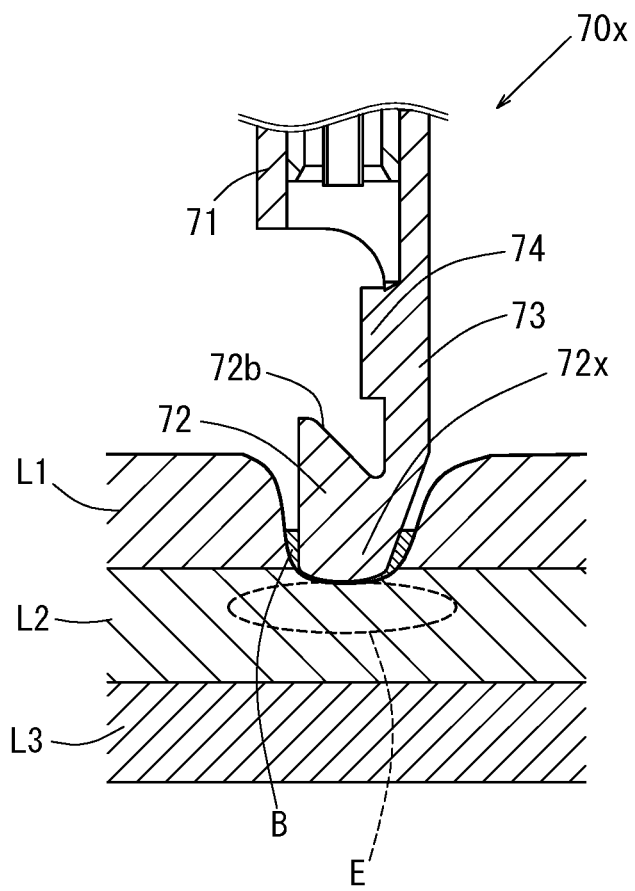
Figure 9A:
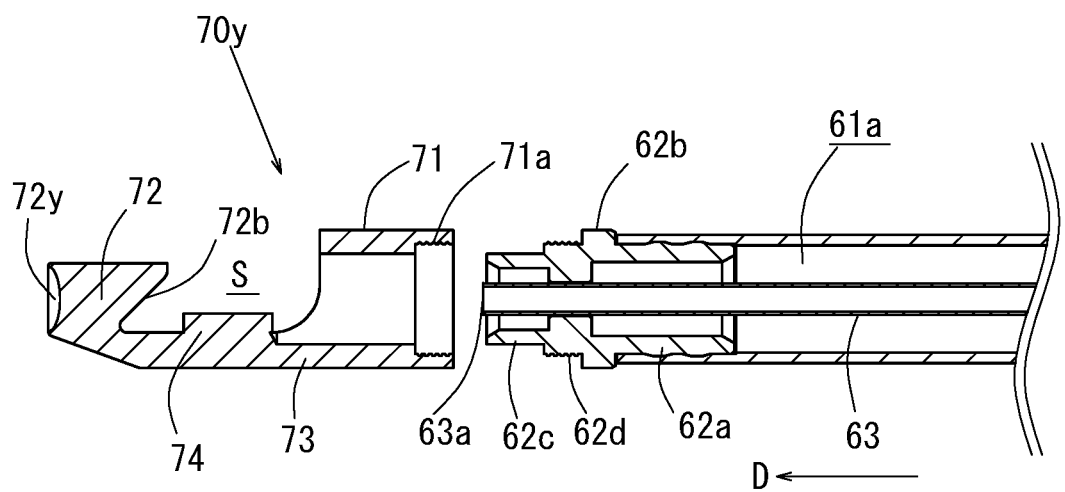
FIGS. 9 A and 9B illustrate a laser tip in still another embodiment.
Figure 9B:
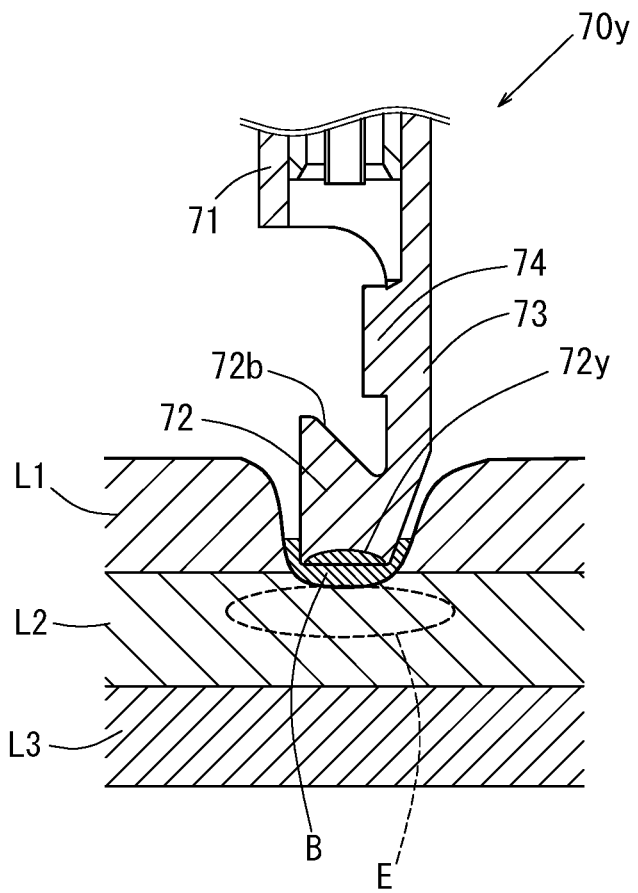

FIG. 8A and FIG. 8B illustrate a case where the contact surface is mildly protruding. FIG. 9 A and FIG. 9B illustrate a case where the contact surface is mildly recessed. In more detail, FIG. 8A is a cross-sectional view of a laser tip 70*x* in which the contact surface is mildly protruding. FIG. 8B is a schematic cross-sectional view showing a method for stopping the bleeding from the bleeding site E by use of the laser tip 70*x*. FIG. 9A is a cross-sectional view of a laser tip 70*y* in which the contact surface is mildly recessed. FIG. 9B is a schematic cross-sectional view showing a method for stopping the bleeding from the bleeding site E by use of the laser tip 70*y*. The bleeding site E is a blood vessel running in the submucosa L2 located between the mucosal layer L1 and muscular layer L3.

As shown in FIG. 8A, the contact surface formed at a front surface of the laser tip 70*x* is a protruding contact surface 72*x*, which is protruding forward and mildly curved. The protruding contact surface 72*x* has a radius of curvature of 15 mm.

In the case where the contact protruding surface 72*x* is put into contact with the bleeding site E, the biological tissue is deformed in accordance with the curved surface, and thus the amount of the blood B located between the bleeding site E and the protruding contact surface 72*x* is decreased. As a result, the blood B is coagulated with certainty and the bleeding from the bleeding site E is stopped (see FIG. 8B).

Unlike in the laser tip 70, an end of the protruding contact surface 70*x* does not have a right angle or an acute angle. Therefore, the biological tissue in the vicinity of the bleeding site E is not damaged by such an acute or right-angled end.

As shown in FIG. 9A, the contact surface formed at a front surface of the laser tip 70*y* is a recessed contact surface 72*y*, which is recessed rearward and mildly curved. The recessed contact surface 72*y* has a radius of curvature of 15 mm.

In the case where the recessed contact surface 72*y* is put into contact with the bleeding site E, the blood B is held between the recessed contact surface 72*y* and the bleeding site E. The blood B held here is put into contact with the recessed contact surface 72*y*, which is heated. Thus, the blood B is coagulated with certainty, and the bleeding from the bleeding site E is stopped (see FIG. 9B).

The laser tips 70, 70*x* and 70*y* structured as described above each include the laser transmission tube attaching portion 71 detachable from the laser radiation opening 63*a*, the contact portion 72 contactable with a biological tissue, and the coupler 73 coupling a part of the contact portion 72 and the laser transmission tube attaching portion 71 to each other. The contact portion 72 is located away from the laser transmission tube attaching portion 71 by the open space S, and to the front of the laser transmission tube attaching portion 71 in a direction in which the laser light 57*a* from the laser radiation opening 63*a* is directed. With such a structure, the laser tips 70, 70*x* and 70*y* are attachable to the laser radiation opening 63*a*, at the tip end of the hollow waveguide tube 63, through which the laser light 57*a* is directed. The reflective surface 72*b* reflecting the laser light 57*a*, directed forward from the laser radiation opening 63*a*, toward the coupler 73 is provided at the rear end of the contact portion 72. With such a structure, a surgery is performed safely for a laser treatment, and bleeding, if occurred, is stopped.

This will be described in more detail. The reflective surface 72*b* reflects the laser light 57*a*, directed from the laser radiation opening 63*a*, toward the coupler 73. This prevents the reflected laser light 57*a* from being directed toward a normal tissue, which is not a target of surgery. Thus, the normal biological tissue is prevented from being damaged.

The laser light 57*a* is directed toward the contact portion 72. As a result, the contact portion 72 absorbs the energy of the laser light 57*a* and is heated. The contact portion 72, thus heated, is put into contact with, for example, the bleeding site E, so that the bleeding from the bleeding site E is stopped.

The coupler 73 couples a part of the contact portion 72 and the laser transmission tube attaching portion 71 to each other, with the open space S being provided between the contact portion 72 and the laser transmission tube attaching portion 71. The open space S is formed between the contact portion 72 and the laser transmission tube attaching portion 71 in a direction perpendicular to the direction in which the laser light 57*a* is directed. With such a structure, the submucosa L2, which is fibrotic and difficult to be cut, is held and located in the open space S. Thus, the laser light 57*a* is directed toward the submucosa L2 and thus cuts the tissue in the submucosa L2 with certainty.

The contact portion 72 absorbing the laser light 57*a* is provided to the front of the laser radiation opening 63*a*. Thus, the contact portion 72 has a so-called back-stop function of preventing a region to the front of the contact portion 72 from being irradiated with the laser light 57*a*. Even in the case where a tissue having a thin tissue wall and the vicinity thereof (e.g., the muscular layer L3 such as colon or the like) is to be peeled off, the surgery may be performed with no risk of making a perforation.

As described above, the laser tips 70, 70*x* and 70*y* stop the bleeding from the bleeding site E, prevent a normal tissue from being damaged as a result of being irradiated with the reflected laser light 57*a*, and prevent perforation from being made by the laser light 57*a*. Therefore, the surgery is performed safely.

The reflective surface 72*b* makes an acute angle with respect to the coupler 73. Therefore, the laser light 57*a* reflected by the reflective surface 72*b* is directed toward the coupler 73 with certainty. Thus, a normal tissue is prevented from being irradiated with the reflected light inadvertently.

The reflective surface 72*b* and the coupler 73 make an acute angle with respect to each other. Therefore, in order to hold and locate the submucosa L2 in the open space S formed between the contact portion 72 and the laser transmission tube attaching portion 71, the tissue in the submucosa L2 is hooked by the reflective surface 72*b*. With such an arrangement, the tissue in the submucosa L2, even if being made fibrotic, is held stably and certainly, and thus is irradiated with the laser light 57*a* with certainty. This allows the affected tissue T to be peeled off without making a perforation in, for example, the muscular layer L3.

In order to peel off a tissue, the contact portion 72 of each of the laser tips 70, 70*x* and 70*y* is inserted into the tissue, so that the biological tissue is stably held in a space defined by the reflective surface 72*b*, the coupler 73 and the laser radiation opening 63*a*. The laser light 57*a* is directed while the laser tip 70, 70*x* or 70*y* is moved in the left-right direction as seen from the operator, or toward the operator. Therefore, even a tissue that has become fibrotic and thus would be otherwise difficult to be cut is easily cut and peeled off.

The protruding contact surface 72*x* or the recessed contact surface 72*y* having a radius of curvature of 10 mm or larger, or the flat contact surface 72*a*, is provided at a front surface of the contact portion 72. Therefore, the bleeding is stopped without enlarging the damaged region.

This will be described in more detail. In the case where, for example, the protruding contact surface 72*x* having a radius of curvature of +10 mm or larger or the flat contact surface 72*a* is provided at the front surface of the contact portion 72, the contact surface 72*a* or the protruding contact surface 72*x* is pressed to the bleeding site E with certainty, and the laser light 57*a* is directed toward the contact surface 72*a* or the protruding contact surface 72*x*. The contact surface 72*a* or the protruding contact surface 72*x* of the contact portion 72 absorbs the energy of the laser light 57*a* and thus is heated. Therefore, the blood B at the bleeding site E, which is in contact with the contact surface 72*a* or the protruding contact surface 72*x*, and in the vicinity of the bleeding site E is coagulated. Thus, the bleeding from the bleeding site E is stopped with certainty.

In the case where the recessed contact surface 72*y* having a radius of curvature of −10 mm or larger is provided, the recessed contact surface 72*y* is pressed to the bleeding site E, and thus the blood B from the bleeding site E is held in the recessed contact portion 72*y*. The laser light 57*a* is directed toward the recessed contact portion 72*y*, so that the blood B held in the recessed contact portion 72*y* is coagulated by the contact portion 72 heated by the laser light 57*a*. Thus, the bleeding from the bleeding site E is stopped.

The action of stopping the bleeding is different in accordance with the radius of curvature of the contact surface (72*x*, 72*y*) at the front surface of the contact portion 72, or in accordance with whether the contact surface is flat (72*a*) or not. Among the contact portions 72 having different contact surfaces, an appropriate contact portion may be used in accordance with the site of bleeding or the state of bleeding.

The protrusion 74 having a protruding cross-section as seen in the optical axis direction D is provided so as to protrude from the coupler 73 toward the optical axis of the laser light 57*a* directed from the laser radiation opening 63*a*. Therefore, a tissue in the submucosa L2 is held at a predetermined position in the open space S, and thus the tissue in the submucosa L2 is irradiated with the laser light 57*a* with certainty.

This will be described in more detail. In the case where the tissue in the submucosa L2 is held by a coupler with no protrusion 74 and the contact portion 72, it is difficult to locate the tissue in the submucosa L2 at a position to which the laser light 57*a* is to be directed. In the case where the protrusion 74 protruding toward the optical axis of the laser light 57*a* is provided on the coupler 73, the tissue in the submucosa L2 is allowed to be located on the protrusion 74.

Thus, the laser light 57a is directed toward a desired position in the biological tissue, and the tissue in the submucosa L2 is cut at the desired position.

The protrusion 74 has a triangular cross-section having an optical axis-side apex of an acute angle. Therefore, the protrusion 74 assists the cutting of the tissue in the submucosa L2.

The reflective surface 72b is coated so as to decrease the reflectance of the laser light 57a. This increases the energy of the laser light 57a that is absorbed by the contact portion 72. Thus, the contact portion 72 is efficiently heated. In the case where the contact portion 72 is put into contact with a damaged site, namely, a bleeding site, the bleeding is stopped with certainty.

The contact portion 72 is coated so as to prevent unintentional adhesion with a biological tissue. Therefore, the contact surface 72a in contact with the biological tissue is prevented from being bonded with the biological tissue. This prevents the bleeding site E from being damaged when the contact surface 72a is separated from the bleeding site E after the bleeding from the bleeding site E is stopped.

Now, another embodiment according to the present invention will be described with reference to the drawings.

Figure 10:
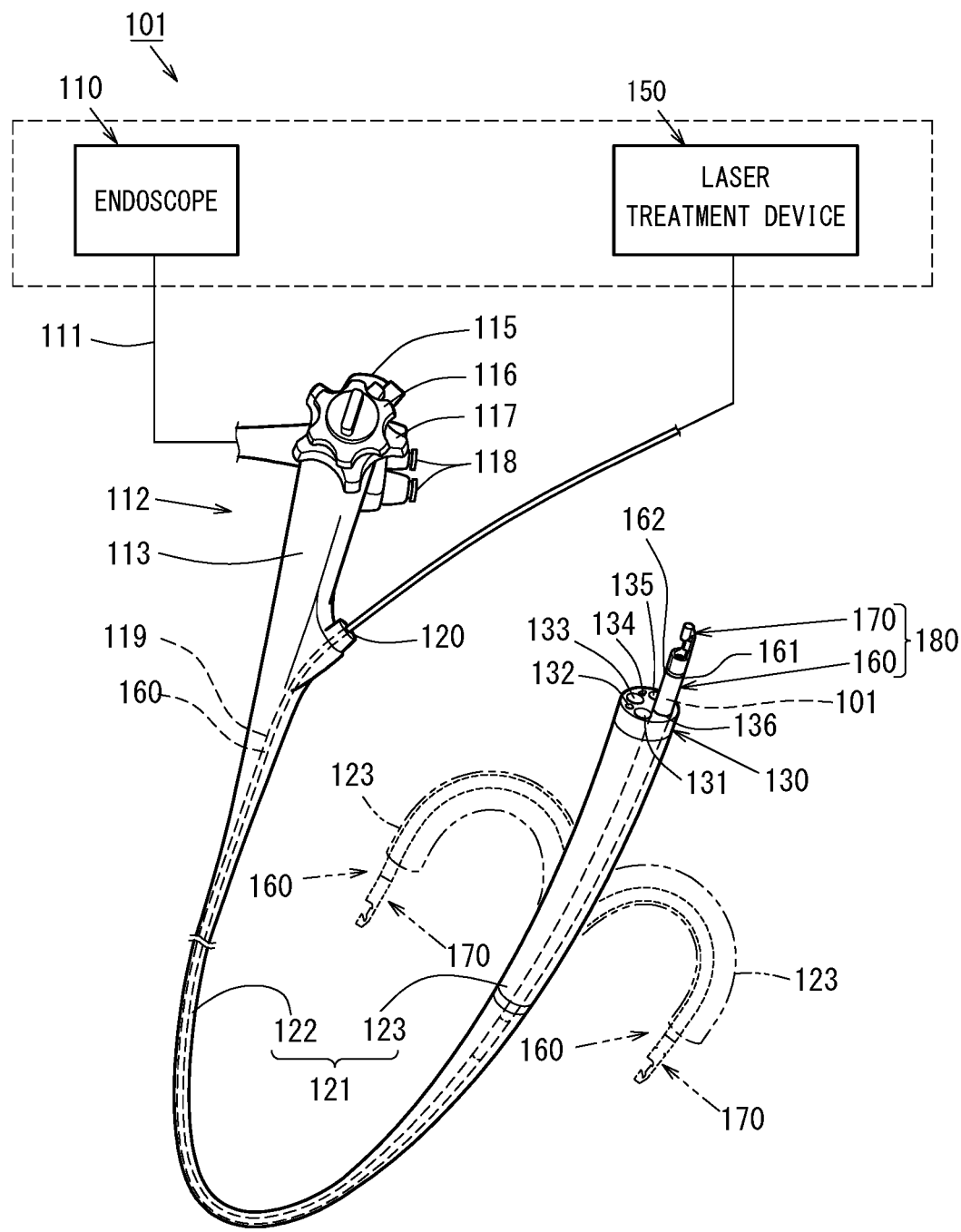
FIG. 10 is a schematic structural view of a laser treatment system including an endoscope device and a laser treatment device in still another embodiment.
Figure 11:
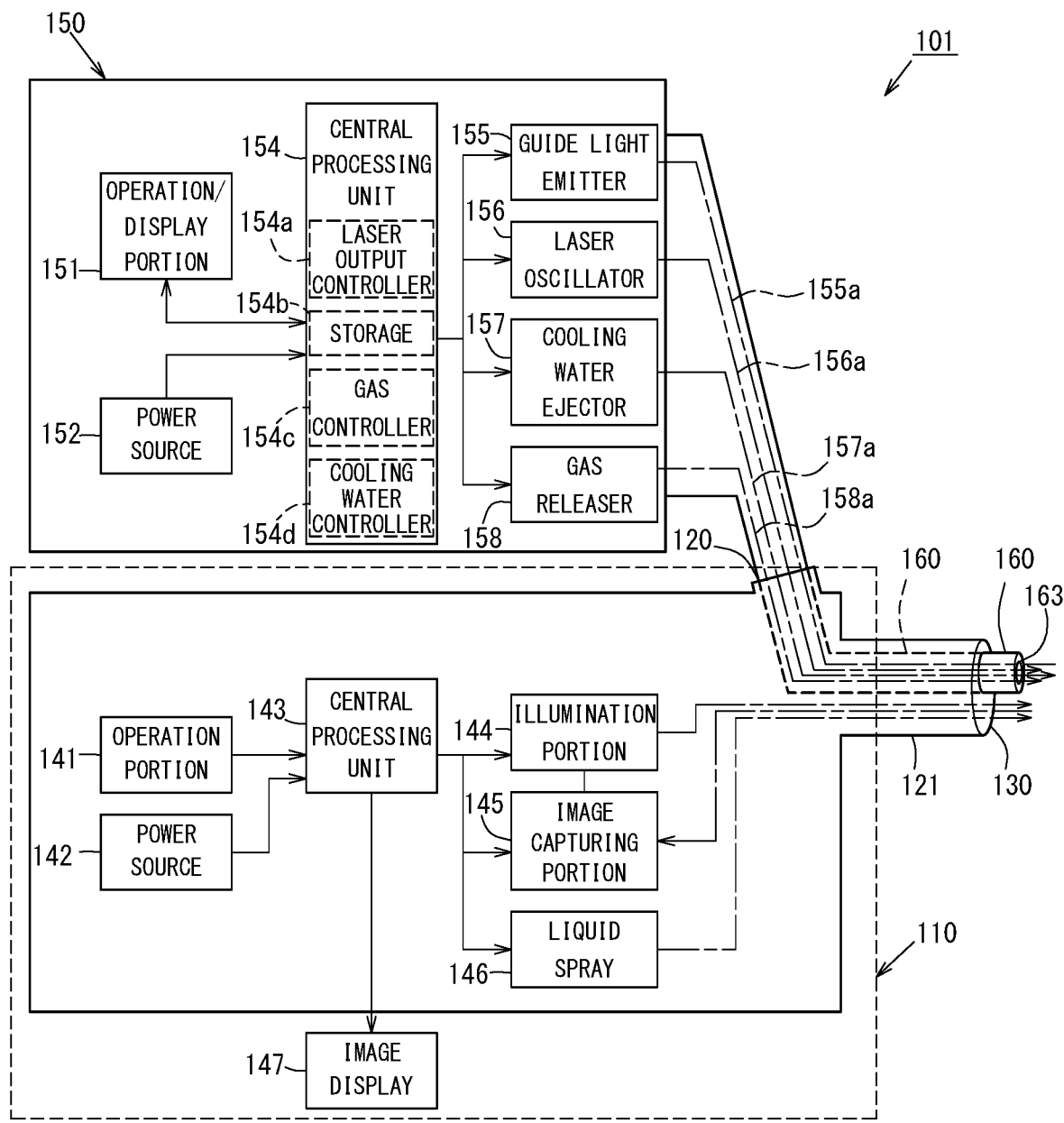
FIG. 11 is a block diagram showing a structure of the endoscope device and the laser treatment device.

FIG. 10 is a structural view schematically showing a structure of a laser treatment system 101 including an endoscope device 110 and a laser treatment device 150. FIG. 11 is a block diagram showing a structure of the endoscope device 110 and the laser treatment device 150.

The laser treatment system 101 includes the endoscope device 110 and the laser treatment device 150. As shown in FIG. 10, the endoscope device 110 includes a device main body and an operation unit 112 connected with the device main body via a connection cable 111.

The operation unit 112 mainly includes an operation portion 113 and an endoscope tube 121.

The operation portion 113 includes an eye contact portion 115, a top/bottom angle knob 116, a left/right angle knob 117, an operation button 118, a device insertion opening 120, and the like.

The operation button 118 receives an operation input such as air transmission, liquid transmission, absorption, zooming or the like.

The endoscope tube 121 includes a flexible tube portion 122, a curved tube portion 123 and a tip portion 130 provided in this order from a base end (rear end) to a tip end thereof. The endoscope tube 121 has a device insertion path 119 formed therein. The device insertion path 119 is continuous from the device insertion opening 120 to a device outlet 136 of the tip portion 130. The device insertion path 119 acts as a treatment device insertion path through which a treatment device such as a forceps, a laser transmission tube 160 or the like is insertable.

In FIG. 10, the laser treatment system 101 is shown as having a diameter increasing from the middle of the flexible tube 122 to a tip end of the curved tube 123. The treatment system 101 is shown in this way merely to make the structure thereof easy to understand. In actuality, the endoscope tube 121 has a constant diameter that is suitable for the endoscope tube 121 to be inserted into a biological organ such as esophagus, stomach, intestine or the like.

The flexible tube 122 has a cylindrical shape that is appropriately curved. An appropriate treatment device such as a forceps of the like may be inserted from the device insertion opening 120 to the tip portion 130. In this embodiment, the laser transmission tube 160 is inserted as the treatment device into the flexible tube 122 in the state where a laser treatment device 150 is connected with the laser transmission tube 160. A laser treatment tool 180 includes the laser transmission tube 160 and a laser tip 170 attachable to a tip end of the laser transmission tube 160.

The curved tube 123 may be curved in an up-down direction by an operation made on the top/bottom angle knob 116, and may be curved in a left-right direction by an operation made on the left/right angle knob 117.

The tip portion 130 includes light guides 131 and 135, a sub liquid transmission opening 132, a lens 133, a nozzle 134, and the device outlet 136.

The light guides 131 and 135 are illumination portions providing illumination light for image capturing. The light guides 131 and 135 illuminate the inside of the body to which light would not reach otherwise, so that the inside of the body is observed and operated on.

Through the sub liquid transmission opening 132, a liquid such as a washing liquid usable to wash an affected site, a dye liquid or the like is released.

The lens 133 includes a lens collecting the illumination light provided by the light guides 131 and 135 or the like to acquire a captured image, and an image capturing element located to the rear of the lens.

The nozzle 134 is a portion releasing, for example, the washing liquid usable to wash the lens 133, toward the lens 133.

The device outlet 136 is an outlet of the treatment device such as, for example, the laser transmission tube 160 attached to the laser treatment device 150. The laser transmission tube 160 is longer than a device insertion path length, which is the entire length of the endoscope tube 121. The laser transmission tube 160 will be described in detail below.

A shown in FIG. 11, the endoscope device 110 includes an operation portion 141, a power source 142, a central processing unit 143, an illumination portion 144, an image capturing portion 145, a liquid spray 146, and an image display 147.

The operation portion 141 transmits an operation input provided by the operation portion 113 (see FIG. 10) to the central processing unit 143. Namely, the operation portion 141 transmits an operation of curving the curved tube 123 made by an operation on the top/bottom angle knob 116 or the left/right angle knob 117, an operation of pressing the operation button 118 or the like. Alternatively, separately from the operation unit 112, another operation portion may be provided in, for example, a controller main body (not shown) of the endoscope device 110, so that an operation of setting an amount of illumination light, capturing and storing a still image, or the like is transmitted to the central processing unit 143.

The power source 142 supplies power for operations to components such as the central processing unit 143 and the like. The central processing unit 143 executes various control operations on the components.

The illumination portion 144 provides the illumination light from the light guides 131 and 135 (see FIG. 10).

The image capturing portion 145 captures an image, transmitted from the lens 133 and the image capturing element (see FIG. 10) located to the rear of the lens 133, to provide a captured image necessary for the surgery, or to perform image processing. Such captured images are provided continuously in real time, so that the operator performs surgery smoothly.

The liquid spray 146 sprays the liquid from the sub liquid transmission opening 132. The liquid spray 146 also sprays the liquid from the nozzle 134. The image capturing portion 145 may be provided in the vicinity of the tip portion 130, or in the controller main body (not shown) of the endoscope device 110.

The image display 147 displays an image in accordance with a signal transmitted from the central processing unit 143. The image encompasses the captured image captured by the image capturing portion 145. Therefore, the operator may perform the surgery while checking the captured images displayed on the image display 147 in real time.

As shown in FIG. 11, the laser treatment device 150 includes an operation/display portion 151, a power source 152, a central processing unit 154, a guide light emitter 155, a laser oscillator 156, a cooling water ejector 157, and a gas releaser 158.

The operation/display portion 151 receives an operation input such as a laser output setting, an operation mode change or the like, transmits such an input signal to the central processing unit 154, receives a display signal on laser output conditions, a device operation state or the like from the central processing unit 154, and displays appropriate information.

The power source 152 supplies the power for operations to components such as the central processing unit 154 and the like.

The central processing unit 154 executes various control operations on the components. The central processing unit 154 includes a laser output controller 154a, a storage 154b, a gas controller 154c and a cooling water controller 154d.

The laser output controller 154a controls an output value of laser light 156a to be provided by the laser oscillator 156 in accordance with the output or the operation mode set by the operation/display portion 151. The storage 154b has, stored thereon, control data such as the output setting, the operation mode setting and the like and also appropriate data.

The guide light emitter 155 emits guide light 155a to indicate the position to which the laser light 156a for treatment is to be directed. With the guide light 155a, the position to which the laser light 156a for treatment is to be directed is checked.

The laser oscillator 157 oscillates the laser light 156a usable for a surgery. In this embodiment, the laser light 156a is carbon dioxide gas laser light. An operation such as setting of the radiation strength of the carbon dioxide gas laser light, start/stop of the radiation or the like is performed by a manual operation on the operation/display portion 151 and by a control output provided by the central processing unit 154. A part of, or the entirety of, the manual operation may be replaced with a stomping operation made by use of a foot controller (not shown) that is communicable with the laser treatment device 150 to control the laser treatment device 150.

The guide light 155a provided by the guide light emitter 155 and the laser light 156a oscillated by the laser oscillator 156 are both transmitted by one laser transmission tube 160.

The cooling water ejector 157 supplies cooling water 157a usable to cool the hollow waveguide tube 162 heated by the laser light 156a, and recovers the supplied cooling water 157a. The cooling water 157a may be circulated after being recovered and supplied again. In this embodiment, the cooling water 157a is distilled water. The amount of the cooling water 157a to be released is controlled by a manual operation on the operation/display portion 151 and by a control output provided by the central processing unit 154.

The cooling water 157a may be replaced with tap water, gas such as air, nitrogen gas or the like, or a gel-like substance.

The gas releaser 158 shown in FIG. 11 releases release gas 158a to flow into the laser transmission tube 160. In this embodiment, the release gas 158a is compressed air.

Now, with reference to FIG. 12 through FIG. 15, a structure of the laser transmission tube 160 and a structure of the laser tip 170 attachable to the tip end of the laser transmission tube 160 will be described.

Figure 12:
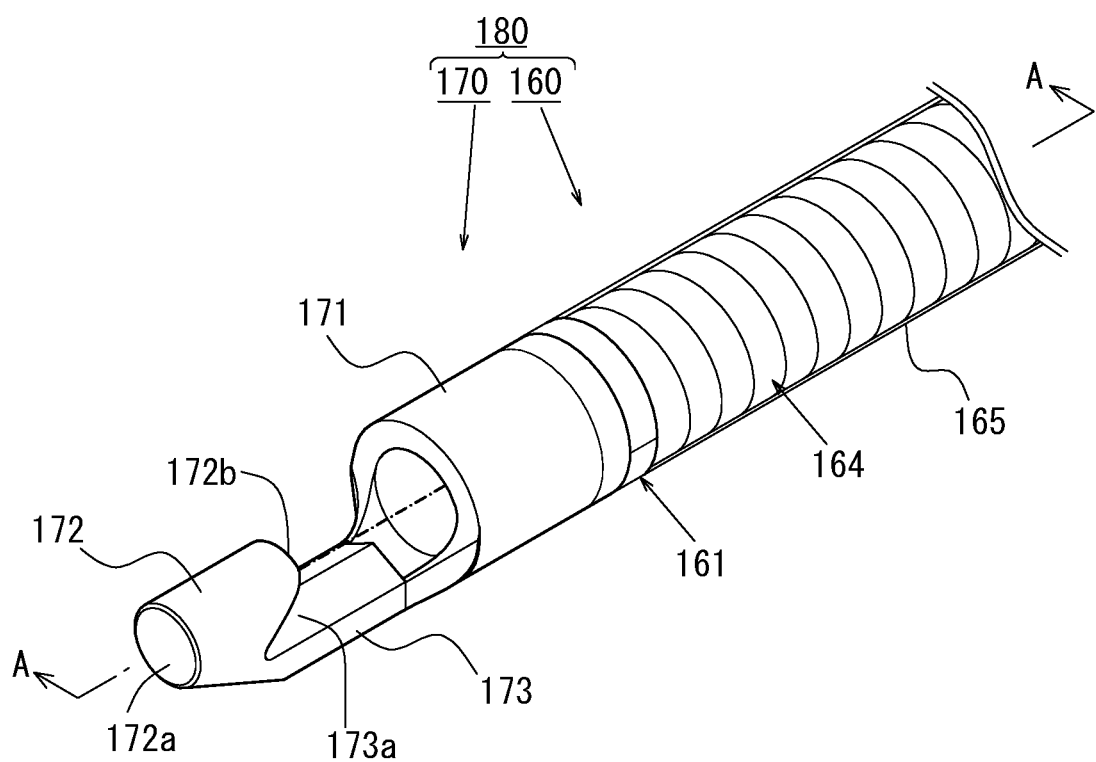
FIG. 12 is an enlarged perspective view of a tip end of a laser transmission tube and a laser tip.
Figure 13:
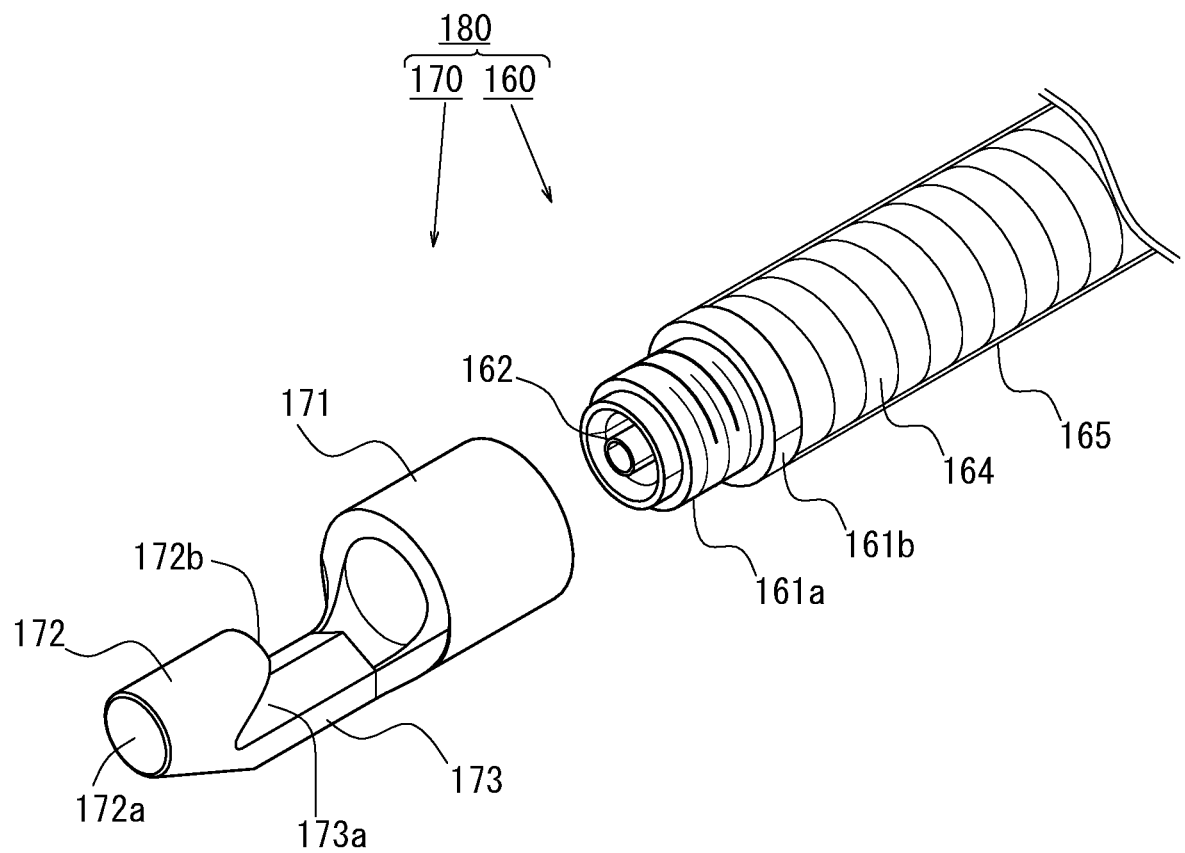
FIG. 13 is an enlarged exploded perspective view of the laser tip and the laser transmission tube in a state where the laser tip is detached therefrom.

FIG. 12 is an enlarged perspective view of the tip end of the laser transmission tube 160, more specifically, is a schematic enlarged perspective view of the laser transmission tube 160 having the laser tip 170 attached to the tip end thereof. FIG. 13 is a schematic enlarged perspective view of the laser transmission tube 160 in a state where the laser tip 170 is detached from the laser transmission tube 160. FIG. 14 A, FIG. 14B, FIG. 15A and FIG. 15B each illustrate the laser tip 170

Figure 14A:
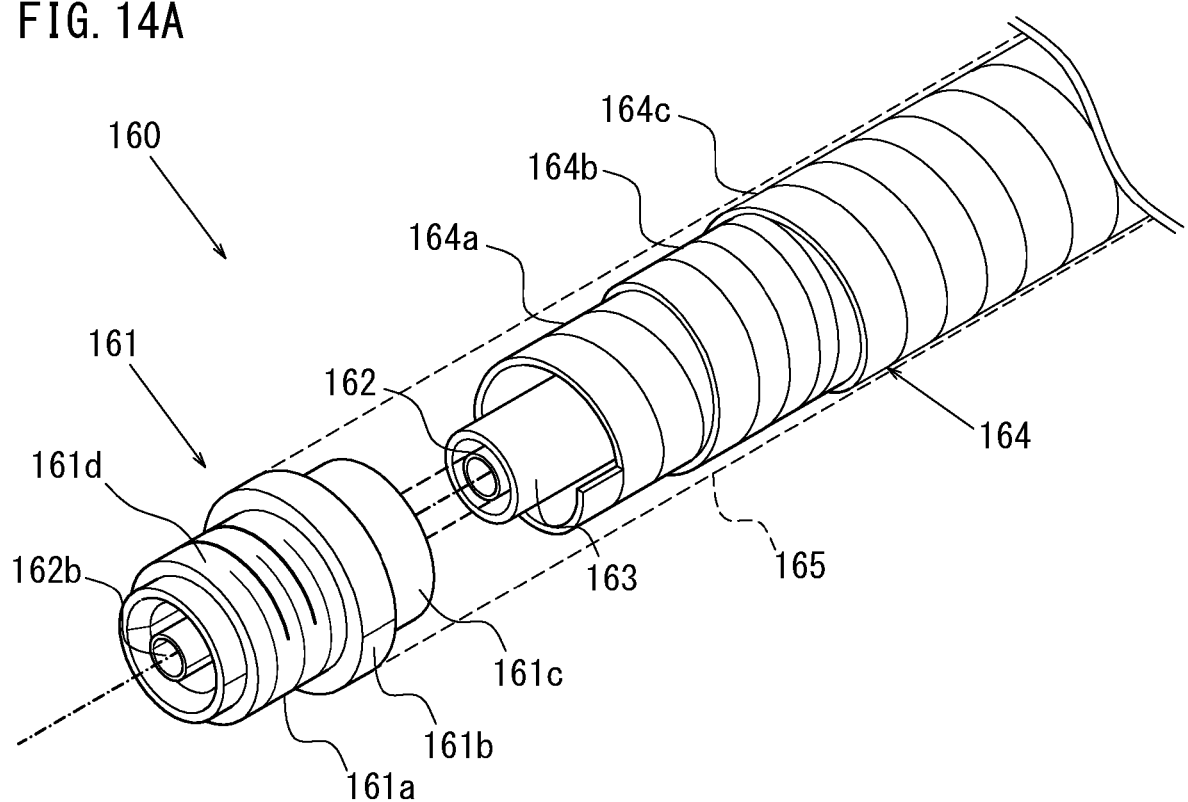
FIGS. 14A and 14B illustrate the laser transmission tube.
Figure 14B:
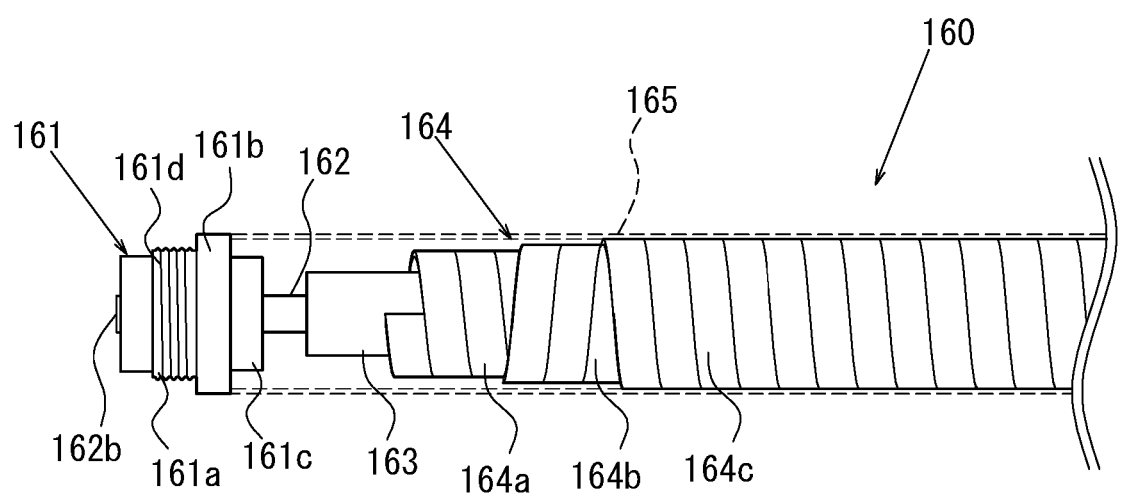

FIG. 14A, FIG. 14B, FIG. 15A and FIG. 15B will be described in more detail. FIG. 14A is a schematic perspective view of the tip end of the laser transmission tube 160. FIG. 14B is a side view of the laser transmission tube 160 shown in FIG. 14A. In FIG. 14A and FIG. 14B, in order to clearly show the structure of the laser transmission tube 160, an outer casing 164 is partially omitted, and a hollow waveguide tube 162 and an outer tube 165 are partially represented with the dashed line to indicate that components provided inside the hollow waveguide tube 162 and an outer tube 165 are shown.

Figure 15A:
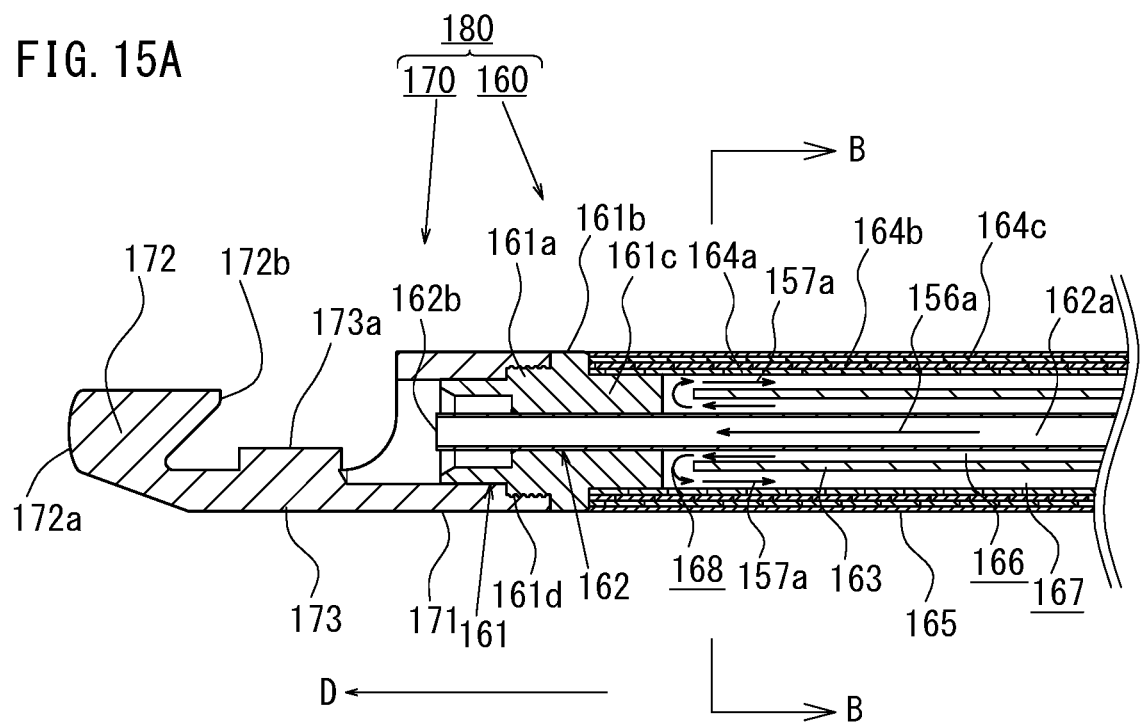
FIGS. 15A and 15B illustrate the laser transmission tube.
Figure 15B:
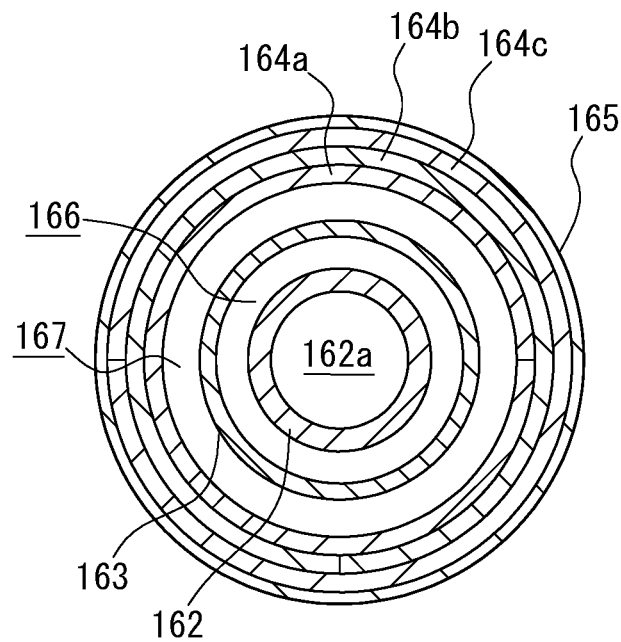

FIG. 15A is a cross-sectional view taken along line A-A in FIG. 12. FIG. 15B is a cross-sectional view taken along line B-B in FIG. 15A.

The laser transmission tube 160 is a hollow cylindrical body longer than the endoscope tube 121. As shown in FIG. 12 through FIG. 15, the laser transmission tube 160 includes an attaching portion 161 having a tip end to which the laser tip 170 is attachable, the hollow waveguide tube 162 guiding the laser light 156a, a water path forming tube 163 enclosing an outer circumferential surface of the hollow waveguide tube 162, the outer casing 164 enclosing an outer circumferential surface of the water path forming tube 163, and the outer tube 165.

As shown in FIG. 13 through FIG. 15, the attaching portion 161 includes a laser tip attaching portion 161a, a tube coupler 161b, and an outer casing 164 securing portion 161c, which are located in this order from the tip end toward a rear end of the attaching portion 161.

The laser tip attaching portion 161a is a generally cylindrical body secured to the tip end of the laser transmission tube 160, and has a thread 161d, extending in the optical axis direction D, in an outer circumferential surface thereof. The thread 161d is engaged with, and secured to, a thread formed in an inner circumferential surface of an end portion of the laser tip 170.

The tube coupler 161b is a cylindrical body provided at a rear end of the laser tip attaching portion 161a, and has an outer diameter that is larger than an outer diameter of the laser tip attaching portion 161a and is slightly smaller than an inner diameter of the device insertion path 119.

As shown in FIG. 14 A, FIG. 14B, FIG. 15A and FIG. 15B, the outer casing securing portion 161c is a cylindrical body having an outer diameter that is approximately equal to the outer diameter of the laser tip attaching portion 161a described below and having an inner diameter that is approximately equal to the an outer diameter of the hollow waveguide tube 162.

The attaching portion 161 having the above-described structure has a hollow portion formed at a center thereof, and the hollow waveguide tube 162 is secured in the hollow portion.

As described above, the hollow waveguide tube 162 is a cylindrical body having the outer diameter that is approximately equal to the inner diameter of the outer casing securing portion 161c, and having a dielectric thin film (not shown) covering the entirety of an inner circumferential surface thereof. The hollow waveguide tube 162 has a propagation space 162a formed therein and also has a laser radiation opening 162b, through which the laser light 156a is to be directed, formed at a tip end thereof.

The cylindrical body forming the hollow waveguide tube 162 is lengthy and is formed of a material, such as glass or the like, that has a smooth surface and is suitable to be covered with a reflective film of silver or the like and a dielectric thin film. The dielectric thin film is formed of an appropriate material that efficiently reflects laser light such as COP (cyclic olefin polymer), polyimide or the like.

In this embodiment, the inner circumferential surface of the hollow waveguide tube 162 is covered with a reflective film of silver or the like and a dielectric thin film. Therefore, the laser light 156a is propagated in the hollow waveguide tube 162 (propagation space 162a) at a high transmission efficiency.

The hollow waveguide tube 162 having the above-described structure has the outer diameter that is equal to the inner diameter of the outer casing securing portion 161c. Therefore, the hollow waveguide tube 162 is inserted into, and thus is secured to, the outer casing securing portion 161c. As a result, the tip end of the hollow waveguide tube 162 is integrally secured with the rear end of the laser tip attaching portion 161a. Thus, the laser light 156a guided by the hollow waveguide tube 162 is directed from a tip end of the laser tip attaching portion 161a.

In the state where the hollow waveguide tube 162 is secured to the attaching portion 161, the laser radiation opening 162b is secured as slightly protruding from the tip end of the laser tip attaching portion 161a (see FIG. 14B).

As shown in FIG. 13 through FIG. 15, the water path forming tube 163 is a lengthy hollow tube having an inner diameter that is slightly larger than the outer diameter of the hollow waveguide tube 162, and is formed of a flexible resin.

The water path forming tube 163 is secured to a joint main body (not shown) at a rear end thereof, and is slightly shorter than the hollow waveguide tube 162 in a longitudinal direction. Therefore, in the state where the hollow waveguide tube 162 is secured to the outer casing securing portion 161c, a small space (coupling path 168) is formed between a tip end of the water path forming tube 163 and a rear end of the outer casing securing portion 161c. There is a ring-shaped space between the water path forming tube 163 and the outer circumferential surface of the hollow waveguide tube 162. The cooling water 157a, after flowing in the ring-shaped space in a forward direction, passes the small space (coupling path 168) and flows in a ring-shaped space formed between the water path forming tube 163 and an inner circumferential surface of the outer casing 164. Thus, the cooling water 157a is circulated as represented by the arrows in FIG. 15A.

The outer casing 164 is formed of a metal, more specifically, stainless steel, plate that is spirally wound around the outer circumferential surface of the water path forming tube 163. A tip end and a rear end of the outer casing 164 are respectively secured to the outer casing securing portion 161c and the joint main body (not shown). As shown in FIG. 14A and FIG. 14B, the outer casing 164 includes a first layer 164a, a second layer 164b and a third layer 164c partially stacking from a diametrically an inner side to a diametrically outer side.

The first layer 164a is formed of a lengthy metal plate having a predetermined thickness. The metal plate is spirally wound around in a clockwise direction from a tip end to a rear end thereof as seen from the tip end of the outer casing 164, with a predetermined coil gap. The tip end of the first layer 164a is secured to an outer circumferential surface of the outer casing securing portion 161c. The metal plate forming the first layer 164a has a thickness of about 10 μm to about 100 μm.

The second layer 164b is formed of the same type of flat metal plate as that of the first layer 164a. The metal plate is spirally wound around in a counterclockwise direction from a tip end to a rear end thereof as seen from the tip end of the outer casing 164, with a predetermined coil gap. The tip end and the rear end of the second layer 164b are secured to the first layer 164a, which is secured to the outer circumferential surface of the outer casing securing portion 161c.

The third layer 164c is formed of the same type of flat metal plate as that of the first layer 164a. The metal plate is spirally wound around in a clockwise direction from a tip end to a rear end thereof as seen from the tip end of the outer casing 164, with a predetermined coil gap. The tip end and the rear end of the third layer 164c are secured to the second layer 164b.

The first layer 164a, the second layer 164b and the third layer 164c of the outer casing 164 having the above-described structure are spirally wound around. Therefore, even in the case where, for example, the endoscope tube 121 (laser transmission tube 160) is bent, the coil gap is changed to deal with the bending. Namely, the outer casing 164 is flexible.

The first layer 164a and the third layer 164c are spirally wound around in a clockwise direction as seen from the tip end of the outer casing 164, and the second layer 164b sandwiched between the first layer 164a and the third layer 164c is wound around in a counterclockwise direction as seen from the tip end of the outer casing 164.

With such an arrangement, when the rear end of the outer casing 164 is rotated clockwise, the first layer 164a and the third layer 164c are tightened, so that a clockwise torque is transmitted to the tip end of the outer casing 164. Similarly, when the rear end of the outer casing 164 is rotated counterclockwise, the second layer 164b is tightened, so that a counterclockwise torque is transmitted to the tip end of the outer casing 164.

The outer tube 165 is formed of a thermally shrinkable (i.e., shrunk when being heated) and waterproof resin. Therefore, the outer tube 165 is allowed to be a thin film in accordance with the shape of the third layer 164c. In addition, the outer tube 165 is waterproof and therefore, decreases an outer diameter of the laser transmission tube 160.

In the laser transmission tube 160 having the above-described structure, an inner circumferential surface of the water path forming tube 163 encloses the outer circumferential surface of the hollow waveguide tube 162 while being away from the outer circumferential surface of the hollow waveguide tube 162 by a predetermined distance. A first cooling water path 166 is formed between the hollow waveguide tube 162 and the water path forming tube 163. The water path forming tube 163 and the first layer 164a are away from each other by a predetermined distance. A second cooling water path 167 in which the cooling water 157a may flow is formed between the water path forming tube 163 and the first layer 164a. The first cooling water path 166 and the second cooling water path 167 are coupled with each other via the coupling path 168 defined by the outer casing securing portion 161c, the hollow waveguide tube 162 and the first layer 164a.

As described above, rear ends of the first cooling water path 166 and the second cooling water path 167 in communication with each other via the coupling path 168 are each coupled with the cooling water ejector 157 shown in FIG. 11. The cooling water 157a is supplied from the cooling water ejector 157 to the first cooling water path 166. The cooling water 157a, after flowing in the first cooling water path 166, flows into the second cooling water path 167 via the coupling path 168, and is recovered by the cooling water ejector 157.

As shown in FIG. 12, FIG. 13, FIG. 15A and FIG. 15B, the laser tip 170 attachable to the tip end of the laser transmission tube 160 includes a laser transmission tube attaching portion 171 engageable with the attaching portion 161, a contact portion 172 located to the front of the laser transmission tube attaching portion 171 and contactable with a biological tissue, and a coupler 173 coupling a part of the contact portion 172 and the laser transmission tube attaching portion 171 to each other.

The laser tip 170 will be briefly described. The laser transmission tube attaching portion 171 is a cylindrical body having an outer diameter that is approximately equal to an outer diameter of the tube coupler 162b and an inner diameter that is approximately equal to the outer diameter of the laser tip attaching portion 161a. The laser transmission tube attaching portion 171 has a thread, engageable with the thread 161d, in an inner circumferential surface of a rear portion thereof (see FIG. 15A).

The contact portion 172 is a generally cylindrical solid body located to the front of the laser transmission tube attaching portion 171, away from the laser transmission tube attaching portion 171 by a predetermined distance. The contact portion 172 is slightly smaller than the laser transmission tube attaching portion 171, and has, at a tip end thereof, a contact surface 172a contactable with a biological tissue. The laser tip 170 including the contact portion 172 is formed of stainless steel, which absorbs the laser light 156a directed from the laser radiation opening 162b.

In this embodiment, the laser tip 170 is formed of stainless steel. Alternatively, the laser tip 170 may be formed of, for example, another metal material or another heat-resistant material such as a ceramic material or the like as long as the material absorbs the laser light 156a.

The contact portion 172 includes a hook 172b protruding toward the opening in the hollow waveguide tube 162. The contact portion 172 faces the laser radiation opening 162b in the hollow waveguide tube 162. Therefore, the laser light 156a is prevented from advancing beyond the tip end of the contact portion 172.

As shown in FIG. 12 and FIG. 13, the coupler 173, coupling the laser transmission tube attaching portion 171 and the contact portion 172 located to be away from each other by a predetermined distance, couples a bottom part of the laser transmission tube attaching portion 171 and a bottom part of the contact portion 72 to each other.

This will be described in more detail. The coupler 173 has a mountain-shaped cross-section as seen in a direction in which the laser light 156a is directed. The hook 172b of the contact portion 172 hooks and holds submucosa LA2, so that the laser light 156a is directed to cauterize and thus cut the submucosa LA2. The laser tip 170 having the above-described structure has a rotationally asymmetric shape, with the direction in which the laser light 156a is directed being the axis of rotation.

Now, a method for hemostasis usable for endoscopic submucosal dissection (ESD) by use of the laser treatment system 101 will be described.

As described above, in the case where endoscopic submucosal dissection (ESD) is performed by use of the laser treatment system 101, radiation of the laser light 156a may cause bleeding. In such a case, the laser transmission tube 160 having the laser tip 170 attached thereto is inserted into the device insertion path 119 of the operation unit 112. The operation unit 112 is inserted into the body. An image of a portion to the front of the tip portion 130 is captured by the image capturing portion 145 and displayed on the image display 147. Based on this image, the operation unit 112 is inserted until the tip portion 130 reaches a surgery target site. The surgery target site is a lumen of esophagus, stomach or the like, and is a site of a biological body of a human or the like.

The contact portion 172 is put to the bleeding site while the image on the image display 147 is checked. The laser light 156a propagating in the propagation space 162a of the hollow waveguide tube 162 is directed to heat the contact portion 172. The contact surface 172a of the heated contact portion 172 is put into contact with the bleeding site. Thus, the bleeding is stopped.

In this case, the cooling water ejector 157 is actuated, so that the cooling water 157a is circulated in the first cooling water path 166 and the second cooling water path 167. Thus, the hollow waveguide tube 162, which has been heated by the laser light 156a, is cooled by the cooling water 157a. The first cooling water path 166 is configured to contact the outer circumferential surface of the heated hollow waveguide tube 162. Therefore, the hollow waveguide tube 162 is efficiently cooled by the cooling water 157a.

The laser light 156a is $CO_2$ laser light, which is highly absorbable by water, and the cooling water 157a is supplied to the first cooling water path 166 in the vicinity of the water path forming tube 163. The outer circumferential surface of the water path forming tube 163 is enclosed by the outer casing 164. With such a structure, even if the hollow waveguide tube 162 is broken and the laser light 156a propagating in the propagation space 162a leaks (is directed to a wrong site), the endoscope tube 121 is prevented from being damaged. As can be seen, the operation unit 112 is highly safe and highly reliable.

In this embodiment, the laser tip 170 is attached to the laser transmission tube 160, so that a biological tissue, more specifically, a tissue in the submucosa LA2 in the vicinity of the affected tissue T to be peeled off, is cut safely.

Hereinafter, a method for cutting the tissue will be briefly described with reference to FIG. 16A to FIG. 16C.

Figure 16A:
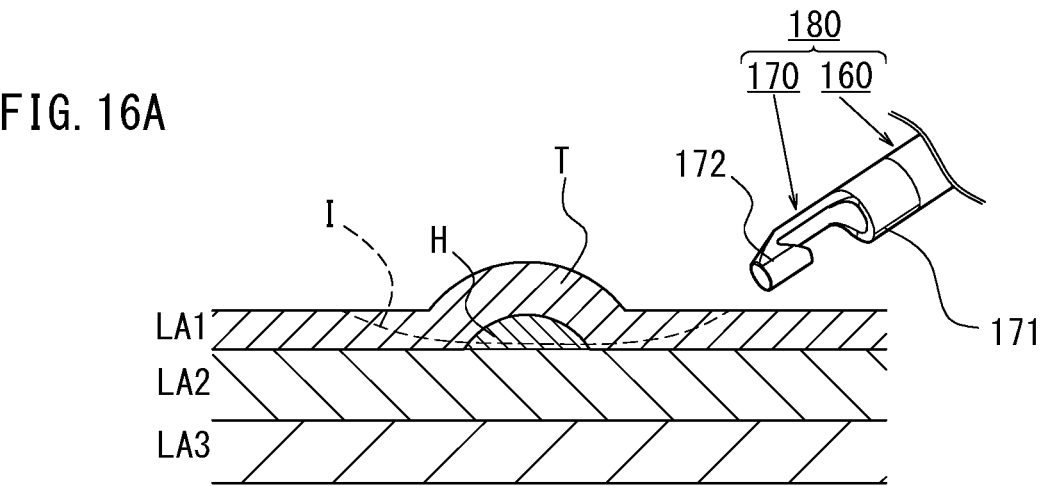
FIGS. 16A to 16C illustrate a method for cutting a biological tissue.
Figure 16B:
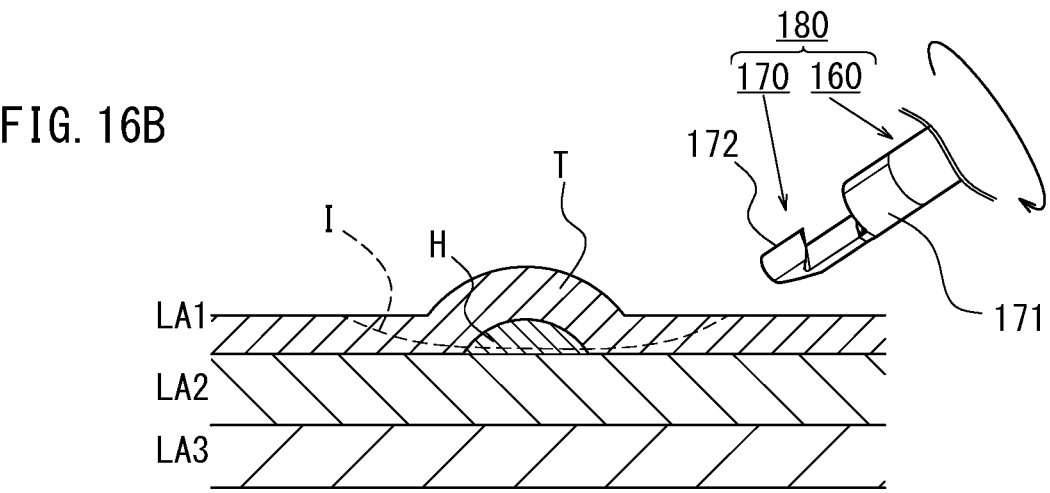
Figure 16C:
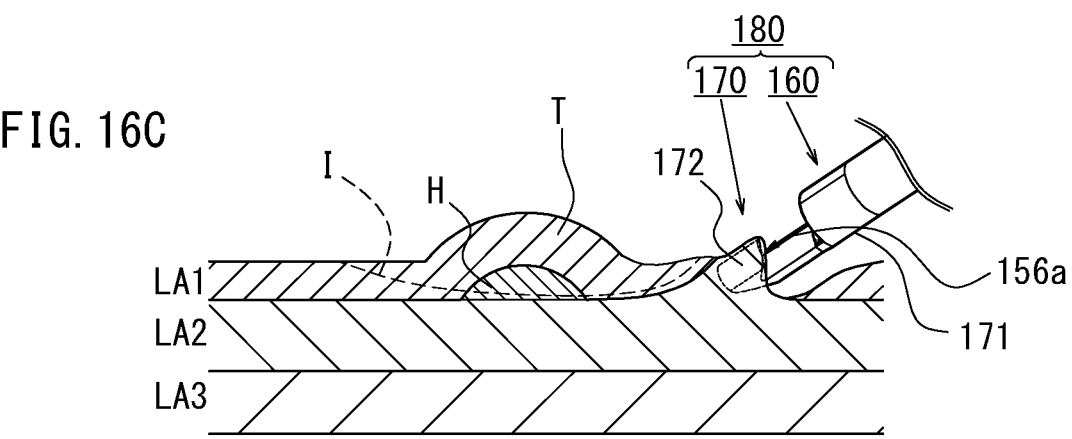

FIG. 16A to FIG. 16C illustrate cutting of the submucosa LA2 by use of the laser tip 170. In more detail, FIG. 16A is a schematic view showing a state where the laser tip 170 is put close to the submucosa LA2 to be cut. FIG. 16B is a schematic view showing a state where the laser tip 170 is put, in an appropriate orientation, close to the submucosa LA2 to be cut. FIG. 16C is a schematic view showing a state where the submucosa LA2 is put on the laser tip 170 and the laser light 156a is directed.

First, the laser light 156a is directed to a plurality of positions enclosing the affected tissue T to mark a range, of a mucosal layer LA1, to be cut off (marking). Next, hyaluronic acid H is injected into the submucosa LA2 below the affected tissue T to pull up the affected tissue T. The laser light 156*a* is directed along the affected tissue T to dissect the mucosal layer LA1 (see FIG. 16A).

Next, the laser transmission tube 160 is pulled out from the device insertion opening 120, the laser tip 170 is attached to the tip end of the laser transmission tube 160, and then the laser transmission tube 160 is inserted again into the device insertion opening 120. At this point, the laser chip 170 is not necessarily oriented in a desired direction. As shown in FIG. 16A, the laser chip 170 may be oriented such that the affected tissue T to be cut is not located between the laser transmission tube attaching portion 171 and the contact portion 172.

In such a case, a rear end of the laser transmission tube 160 is rotated, with the direction in which the laser light 156*a* is directed as the axis of rotation. As a result, as shown in FIG. 16B, the laser tip 170 is oriented in a desired direction. Then, as shown in FIG. 16C, the contact portion 172 is inserted along the dissected mucosal layer LA1, the coupler 173 is used to hook the submucosa LA2 on the hook 172*b* shown in FIG. 13, and the laser light 156*a* is directed to cauterize and thus cut the submucosa LA2.

As described above, while the submucosa LA2 is held by the hook 172*b* shown in FIG. 13 and irradiated with the laser light 156*a*, the laser tip 170 is moved as if mowing the submucosa LA2. The laser light 156*a* is directed in the state where the tissue of the submucosa LA2 is tensioned. In this manner, the tissue of the submucosa LA2 is cut. Thus, the affected tissue T is easily cut away from the submucosa LA2 around the affected tissue T. As a result, the affected tissue T is separated.

As described above, the laser transmission tube 160 includes the hollow waveguide tube 162 guiding the laser light 156*a*, the outer casing 164 formed of a flat metal plate secured to be integral with the hollow waveguide tube 162 and enclosing the outer circumferential surface of the hollow waveguide tube 162, and the attaching portion 161 provided at one end (tip end) of the hollow waveguide tube 162 such that the laser tip 170 is attached thereto. The outer casing 164 has a flexible multi-layer cylindrical structure and acts as a torque transmitter transmitting a torque at the rear end (the other end) thereof to the tip end thereof. With such a structure, the outer diameter of the laser transmission tube 160 is decreased. (In this specification and the claims, one end and the other end are one end and the other end in the longitudinal direction.)

This will be described in more detail. The outer casing 164 formed of a flat metal plate has a multi-layer structure and encloses the outer circumferential surface of the hollow waveguide tube 162. Therefore, an outer diameter of the outer casing 164, which corresponds to the thickness of the metal plate, is the outer diameter of the laser transmission tube 160. Namely, the outer diameter of the laser transmission tube 160 is the thickness of the outer casing 164. Thus, the outer diameter of the laser transmission tube 160 is decreased.

In addition, the outer casing 164 enclosing the outer circumferential surface of the hollow waveguide tube 162 is formed of a metal plate and has a multi-layer structure. Therefore, even if the hollow waveguide tube 162 is damaged, the laser light 156*a*, if leaking from the damaged part, is blocked by the outer casing 164 and is prevented from leaking out of the laser transmission tube 160.

The outer casing 164 is secured to be integral with the hollow waveguide tube 162. Therefore, the rotation of the rear end (the other end) of the outer casing 164 is transmitted to the tip end (one end) of the hollow waveguide tube 162. This allows the one end of the hollow waveguide tube 162 to be rotated by a desired amount. The position of the tip end of the hollow waveguide tube 162 is fine-tuned in a circumferential direction.

With the above-described arrangement, in the case where, for example, the laser tip 170 is attached to the attaching portion 161, when the rear end (the other end) is rotated, the tip end of the outer casing 164 acting as a torque transmitter follows the rotation of the rear end and is rotated. Thus, the orientation of the laser tip 170 is fine-tuned in the circumferential direction. The laser tip 170 is located in a desired orientation.

The outer casing 164 includes the first layer 164*a* spirally wound around the outer circumferential surface of the hollow waveguide tube 162 and the second layer 164*b* spirally wound around an outer circumferential surface of the first layer 164*a* in an opposite direction to the first layer 164*a*. With such a structure, the torque generated by the rotation of the rear end of the laser transmission tube 160 is transmitted to the tip end certainly and accurately.

When, for example, the laser transmission tube 160 is rotated at the rear end thereof in a forward direction, in which the first layer 164*a* is wound, the first layer 164*a* is tightened to the hollow waveguide tube 162. Therefore, the torque in the forward direction is transmitted to the tip end of the laser transmission tube 160.

By contrast, when the laser transmission tube 160 is rotated at the rear end thereof in a direction opposite to the direction in which the first layer 164*a* is wound, the first layer 164*a* is loosened from the hollow waveguide tube 162. However, the second layer 164*b* is tightened to the hollow waveguide tube 162. Therefore, the torque in the reverse direction is transmitted to the tip end of the laser transmission tube 160. In this manner, the torque of the rotation at the rear end of the laser transmission tube 160 is transmitted to the tip end with certainty.

An outer circumferential surface of the outer casing 164 is enclosed by the outer tube 165, which is formed of a resin that is waterproof and slippery. Therefore, while the laser transmission tube 160 is inserted into the device insertion path 119 formed in the endoscope tube 121, no kink is caused to realize smooth insertion and the device insertion path 119 is not damaged.

This will be described in more detail. The outer casing 164 is enclosed by the outer tube 165 formed of a resin. This prevents the outer casing 164 from expanding. In addition, the outer tube 165, which is provided between the outer casing 164 formed of a metal material and the device insertion path 119, prevents the outer casing 164 and the laser transmission tube 160 from being stuck with each other. This allows the laser transmission tube 160 to be smoothly inserted into the device insertion path 119, and prevents the outer casing 164 from damaging the device insertion path 119.

The outer tube 165, which is waterproof, prevents a liquid such as a bodily fluid, blood or the like from entering from the outside of the outer casing 164. Thus, a region inner to the outer casing 164 is protected from being corroded or contaminated with such a liquid.

The outer tube 165 encloses the outer circumferential surface of the outer casing 164. Therefore, even if the hollow waveguide tube 162 is damaged, the outer tube 165 suppresses the outer casing 164 from being deformed. The outer casing 164 suppressed from being deformed prevents, with certainty, the laser light 156*a* from leaking outside.

The outer tube 165 is a thermally shrinkable tube shrunk when being heated. Therefore, the outer casing 164 is easily enclosed by the outer tube 165, and the outer tube 165 is made thin. This allows the outer diameter of the laser transmission tube 160 to be decreased, while the waterproofness is provided.

The first cooling water path 166 in which the cooing water 157*a* may flow along the hollow waveguide tube 162 is provided between the hollow waveguide tube 162 and the outer casing 164. This allows the hollow waveguide tube 162 heated by the laser light 156*a* to be cooled by the cooling water 157*a* flowing in the first cooling water path 166. This improves the durability of the laser transmission tube 160 treating the surgery target site with the laser light 156*a* with certainty.

The first cooling water path 166 and the second cooling water path 167 are provided along the hollow waveguide tube 162, and the coupling path 168 communicating the first cooling water path 166 and the second cooling water path 167 to each other is provided at the tip end (one end) of the water path forming tube 163. With such a structure, the cooling water 157*a* which has flown in one of the first cooling water path 166 and the second cooling water path 167 is allowed to flow to the other of the first cooling water path 166 and the second cooling water path 167 via the coupling path 168. In this manner, the cooling water 157*a* is recovered. The cooling water 157*a* is circulated, and the hollow waveguide tube 162 heated by the laser light 156*a* is efficiently cooled. The cooling water 157*a* is circulated in the first cooling water path 166 or the second cooling water path 167 without leaking to the surgery target site.

The mounting portion in the present invention corresponds to the laser transmission attaching portion 171 in the above-described embodiment; and similarly, the reflective portion corresponds to the reflective surface 72*b*;

the contact surface corresponds to any one of the contact surfaces 72, 72*x* and 72*y*;

the laser oscillator corresponds to the laser oscillator 57;
the endoscope corresponds to the endoscope device 10;
the light guide member corresponds to any one of the hollow waveguide tubes 63 and 162;
the laser tip corresponds to any one of the laser tips 70, 70*x* and 70*y*;
the laser treatment tool corresponds to the laser treatment tool 180;
the laser transmission tube corresponds to the laser transmission tube 160;
the attaching portion corresponds to the laser tip attaching portion 161*a*;
the torque transmitter corresponds to the outer casing 164;
the outer layer protective member corresponds to the outer tube 165;
the cooling medium corresponds to the cooling water 157*a*;
the cooling path corresponds to anyone of the first cooling water path 166 and the second cooling water path 167;
the laser oscillator corresponds to the laser oscillator 156;
the laser treatment device corresponds to the laser treatment device 150; and
the endoscope corresponds to the endoscope device 110.

The present invention is not limited to any of the above-described embodiments, and may be carried out in any of various embodiments.

For example, in the above-described embodiment, the coupler 73 couples a bottom part of the laser transmission tube attaching portion 71 and a bottom part of the contact portion 72 to each other. The coupler 73 does not need to couple the parts as long as the open space S is provided between the laser transmission tube attaching portion 71 and the contact portion 72.

The reflective surface 72*b* may have any structure as long as the laser light 57*a* is reflected toward the coupler 73. The reflective surface 72*b* may be flat or concaved. Alternatively, a plurality of the reflective surfaces 72*b* may be combined. Still alternatively, a prism or the like may be used to refract the laser light 57*a*, and the refracted laser light 57*a* may be reflected toward the coupler 73.

The material used to coat the contact surface 72*a* in order to prevent unintentional adhesion may be any material as long as unintentional adhesion with a biological tissue is prevented. The coating material may be, for example, titanium nitride (TiN), silicon carbide (SiC), silicon nitride, boron nitride (BN) or the like.

In the above-described embodiment, the laser oscillator oscillates carbon dioxide gas laser light. The laser light does not need to be carbon dioxide gas laser light, and may be any other type of laser light.

In the above-described embodiment, the laser transmission tube 60 includes the hollow waveguide tube 62. The laser transmission tube 60 does not need to include such a hollow waveguide tube. For example, any of various laser transmission paths such as, for example, a solid fiber or the like is usable.

The laser light 156*a* is $CO_2$ laser light, which is highly absorbable by water, and the cooling water 157*a* is supplied to the first cooling water path 166 around the hollow waveguide tube 162. With such a structure, even if the hollow waveguide tube 162 is broken and the laser light 156*a* propagating in the propagation space 162*a* leaks (is directed to a wrong site), the outer tube 165 and the endoscope tube 121 are prevented from being damaged by the laser light 156*a* being directed to a wrong site. As can be seen, the operation unit 112 is highly safe and highly reliable.

The cooling water 157*a* is supplied from the cooling water ejector 157*a*, flows in the first cooling water path 166, the coupling path 168 and the second cooling water path 167, and is recovered by the cooling water ejector 157. Namely, the cooling water 157*a* is circulated without leaking outside, and thus may be, for example, distilled water or tap water.

Figure 17:
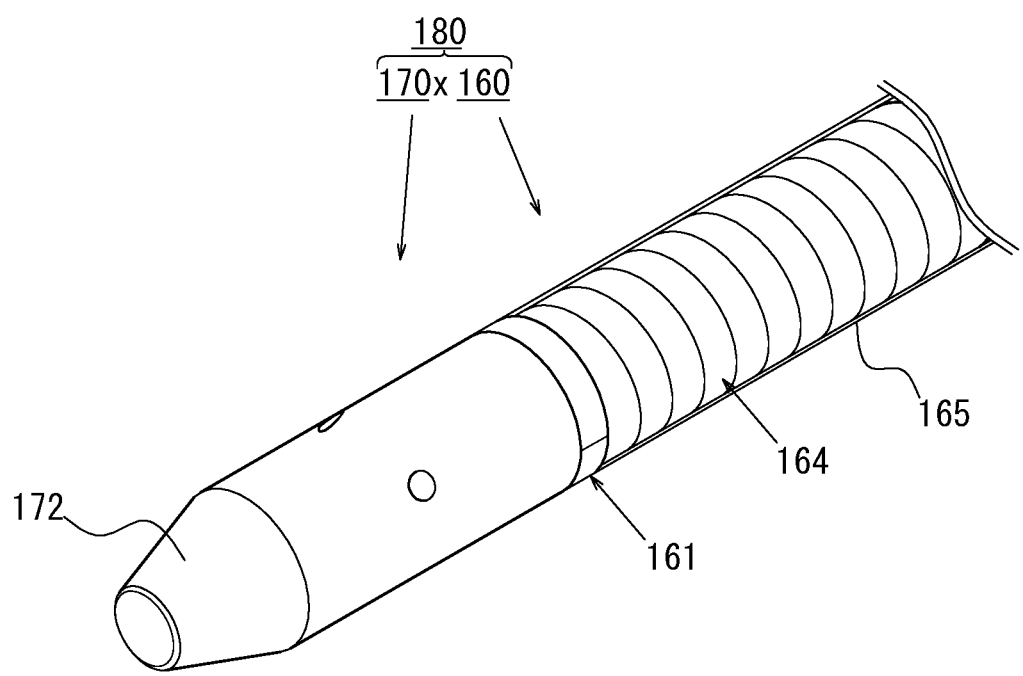
FIG. 17 is an enlarged perspective view of a tip end of a laser transmission tube and a laser tip in still another embodiment.

In the above-described embodiment, the laser tip 170 has a rotationally asymmetric shape, with the direction in which the laser light 156*a* is directed being the axis of rotation. The laser tip 170 does not need to have a rotationally asymmetric shape. For example, as shown in FIG. 17, a hemostatic laser tip 170*x* having a rotationally symmetrical cannonball shape may be used.

Figure 18:
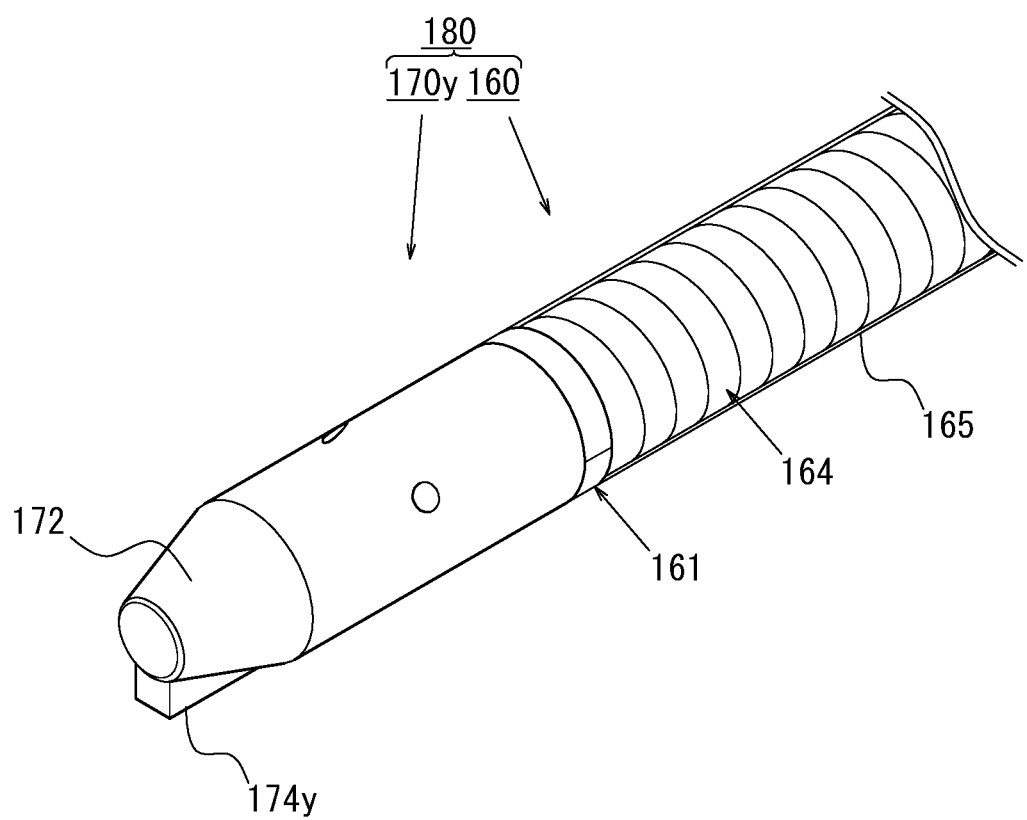
FIG. 18 is an enlarged perspective view of a tip end of a laser transmission tube and a laser tip in still another embodiment.

In the above-described embodiment, the laser tip 170 holds the submucosa LA2 between the laser transmission tube attaching portion 171 and the contact portion 172, so that the submucosa LA2 is directly irradiated with the laser light 156*a*. For example, as shown in FIG. 18, a laser tip 170*y* including a hemostatic portion 174*y* below the contact portion 172 may be used. With such a structure, the laser light 156*a* is directed toward the laser tip 170*y* to heat the hemostatic portion 174*y* and stop bleeding.

The submucosa LA2 may be directed irradiated with the laser light 156*a* without the laser tip 170 being attached to the attaching portion 161. In the case where the laser tip 170 is not attached to the attaching portion 161, the structure of the attaching portion 161 may be appropriately changed.

In the above-described embodiment, the first layer 164*a* and the water path forming tube 163 are separated from each other by a predetermined distance, and the second layer 164*b* is secured. The present invention is not limited to having such a structure. For example, as shown in FIG. 19, the first layer 164*a* and the water path forming tube 163 may be secured, and the first layer 164*a* may not be in close contact with the second layer 164*b*.

Figure 19A:
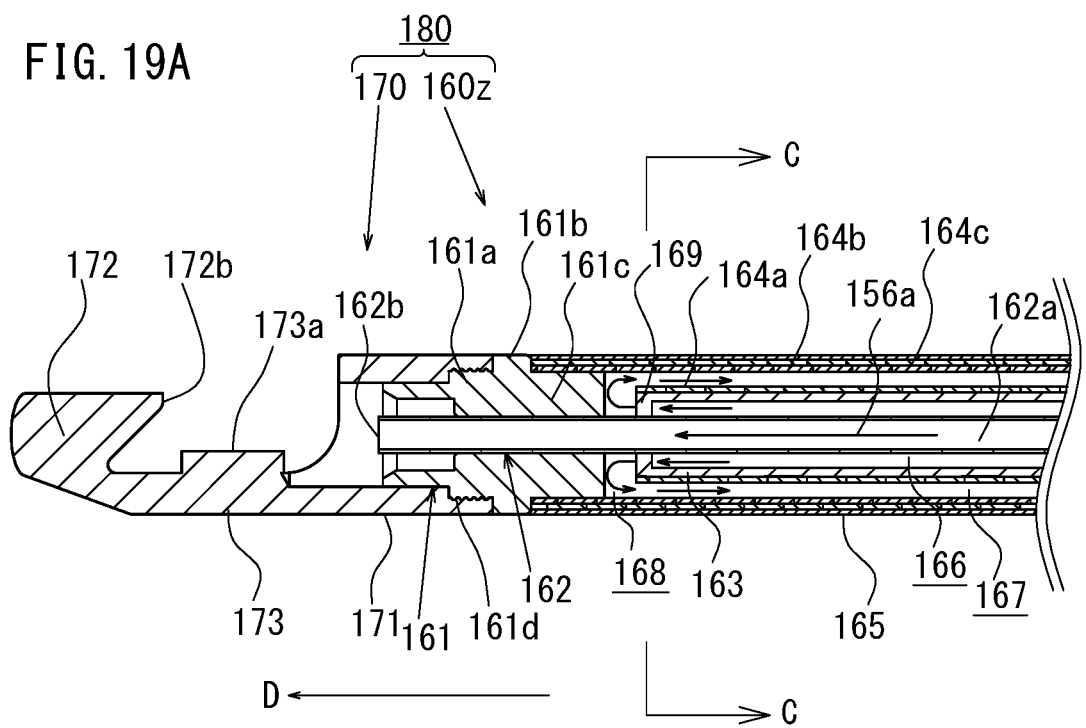
FIGS. 19 A and 19B illustrate a laser transmission tube in still another embodiment.
Figure 19B:
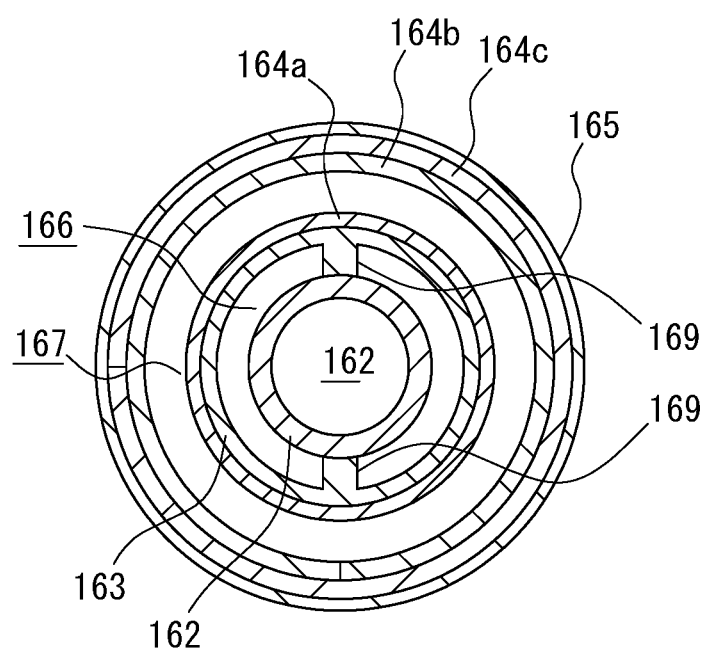

FIG. 19 A and FIG. 19B illustrate a laser transmission tube 160*z* in still another embodiment. In more detail, FIG. 19A is a cross-sectional view corresponding to the cross-sectional view taken along line A-A in FIG. 12. FIG. 19B is a cross-sectional view taken along line C-C in FIG. 19A.

The components of the laser transmission tube 160*z* that are the same as those of the laser transmission tube 160 will bear the same reference signs and descriptions thereof will be omitted.

Specifically in the embodiment shown in FIG. 19A and FIG. 19B the first layer 164*a* encloses the outer circumferential surface of the water path forming tube 163 coupled with the hollow waveguide tube 162 via a coupling path 169. The coupling path 169 is provided at a top end and a bottom end of the tip end of the first layer 164*a*. Therefore, the first layer 164*a* is indirectly secured to the attaching portion 161 via the hollow waveguide tube 162.

With such a structure, when, for example, the rear end of the outer casing 164 is rotated clockwise, the first layer 164*a* and the third layer 164*c* are tightened in a diametrically inner direction, which rotates the attaching portion 161 clockwise. The second layer 164*b* is loosened to expand in a diametrically outer direction. Therefore, the second cooling water path 167 in which the cooling water 157*a* flows from a tip end to a rear end thereof is provided with certainty.

By contrast, when the rear end of the outer casing 164 is rotated counterclockwise, the second layer 164*b* is tightened in a diametrically inner direction, which rotates the attaching portion 161 counterclockwise. As described above, the second layer 164*b* is tightened in a diametrically inner direction. However, since the second layer 164*b* and the third layer 164*c* are secured to each other, the second cooling water path 167 in which the cooling water 157*a* flows from the tip end to the rear end is provided with certainty.

As described above, in the embodiment shown in FIG. 19 A and FIG. 19B, the outer circumferential surface of the water path forming tube 163 is enclosed by the first layer 164*a*. Therefore, the thickness of the outermost layer is made thin, and the second cooling water path 167 is provided with certainty. This allows the hollow waveguide tube 162 to be cooled while the entire outer diameter of the laser transmission tube 160*z* is decreased.

In the above-described embodiment, the first layer 164*a*, the second layer 164*b* and the third layer 164*c* are wound with a predetermined coil gap so as to have a flat surface along the hollow waveguide tube 162. Alternatively, for example, the first layer 164*a*, the second layer 164*b* and the third layer 164*c* may be each wound so as to overlap in the longitudinal direction, more specifically, such that a front portion of one of the layer overlaps a rear portion of another layer.

With such a structure, even if the hollow waveguide tube 162 is broken, the laser light 156*a* is prevented with certainty from leaking. Since the laser light 156*a* is prevented with certainty from leaking, the outer casing 164 may include two layers instead of three layers.

DESCRIPTION OF THE REFERENCE NUMERALS

1, 101 . . . Laser treatment system
10, 110 . . . Endoscope device
50, 150 . . . Laser treatment device
57, 156 . . . Laser oscillator
57*a*, 156*a* . . . Laser light
60, 160 . . . Laser transmission tube
63, 162 . . . Hollow waveguide tube
63*a* . . . Laser radiation opening
70, 70*x*, 70*y*, 170 . . . Laser tip
71 . . . Attaching portion
72 . . . Contact portion
73 . . . Coupler
72*b* . . . Reflective surface
72*a* . . . Contact surface
72*x* . . . Protruding contact surface
72*y* . . . Recessed contact surface
74 . . . Protrusion
157*a* . . . Cooling water
161*a* . . . Laser tip attaching portion
164 . . . Outer casing
164*a* . . . First layer
164*b* . . . Second layer
165 . . . Outer tube
166 . . . First cooling water path
167 . . . Second cooling water path
168 . . . Coupling path
180 . . . Laser treatment tool

What is claimed is:

1. A laser tip attachable to a laser radiation opening provided at a tip end of a laser transmission tube, laser light being directed from the laser radiation opening, the laser tip comprising:
    a mounting portion detachable from the laser radiation opening;
    a contact portion contactable with a biological tissue, the contact portion being provided to the front of the mounting portion in a direction in which the laser light is directed from the laser radiation opening, with an open space being provided between the contact portion and the mounting portion;
    a coupler coupling the contact portion and the mounting portion to each other;
    the contact portion having a reflective portion provided at a rear end thereof, the reflective portion reflecting the laser light, directed forward from the laser radiation opening, toward the coupler,
    wherein the reflective portion has a reflective surface that makes an acute angle with respect to the coupler.

2. A laser tip according to claim 1, the contact portion has a contact surface at a tip end thereof, the contact surface being curved with a radius of curvature of 10 mm or larger or being flat.

3. A laser tip according to claim 1, the coupler is provided with a protrusion protruding toward an optical axis of the laser light directed from the laser radiation opening, the protrusion having a protruding cross-section as seen in a direction of the optical axis.

4. A laser tip according to claim 3, the cross-section of the protrusion has a triangular shape having an optical axis-side apex of an acute angle.

5. A laser tip according to claim 1, a surface of the reflective portion is coated to decrease a reflectance of the laser light.

6. A laser tip according to claim 1, the contact portion is coated to prevent unintentional adhesion with a biological tissue.

7. A laser treatment tool, comprising:
a laser transmission tube guiding laser light to a surgery target site; and
the laser tip according to claim 1.

8. A laser treatment device, comprising:
a laser oscillator oscillating carbon dioxide gas laser light;
a laser transmission tube guiding the laser light oscillated by the laser oscillator to a surgery target site; and
the laser tip according to claim 1.

9. A laser treatment device according to claim 8,
the laser transmission tube including:
   a light guide member guiding the laser light;
   an outer casing formed of a flat metal plate secured to be integral with the light guide member, the outer casing enclosing an outer circumferential surface of the light guide member; and
   an attaching portion provided at one end of the light guide member, the laser tip being attachable to the attaching portion;
the outer casing being a cylindrical body having a flexible multi-layer structure and acting as a torque transmitter transmitting a torque at the other end of the light guide to the one end.

10. A laser treatment device according to claim 9, the outer casing includes:
a first layer spirally wound around the outer circumferential surface of the light guide member; and
a second layer spirally wound around an outer circumferential surface of the first layer in a direction opposite to the first layer.

11. A laser treatment device according to claim 9, an outer circumferential surface of the outer casing is enclosed by an outer layer protective member formed of a waterproof resin.

12. A laser treatment device according to claim 11, the outer layer protective member is formed of a thermally shrinkable tube.

13. A laser treatment device according to claim 9, further comprising a cooling path allowing a cooling medium to flow therein along the light guide member, the cooling path is provided between the light guide member and the outer casing.

14. A laser treatment device according to claim 13, the cooling path includes a first cooling path and a second cooling path formed along the light guide member, the cooling path further includes a coupling path communicating the first cooling path and the second cooling path to each other, the coupling path being provided at one end.

15. A laser treatment system, comprising:
the laser treatment device according to claim 8, and
an endoscope allowing the laser transmission tube to be inserted thereto.

* * * * *

UNITED STATES PATENT AND TRADEMARK OFFICE
CERTIFICATE OF CORRECTION

Page 1 of 1

PATENT NO. : 10,792,102 B2
APPLICATION NO. : 15/924251
DATED : October 6, 2020
INVENTOR(S) : Okagami et al.

It is certified that error appears in the above-identified patent and that said Letters Patent is hereby corrected as shown below:

On the Title Page

Under item (30) "Foreign Application Priority Data," insert:
-- November 22, 2017 (JP).....................................2017-224721. --

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*